(12) United States Patent
Howell et al.

(10) Patent No.: US 6,608,102 B1
(45) Date of Patent: Aug. 19, 2003

(54) PLANT PROANTHOCYANIDIN EXTRACT EFFECTIVE AT INHIBITING ADHERENCE OF BACTERIA WITH P-TYPE FIMBRIAE TO SURFACES

(75) Inventors: Amy B. Howell, Hammonton, NJ (US); Nicholi Vorsa, Atco, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 86 days.

(21) Appl. No.: 09/145,694

(22) Filed: Sep. 2, 1998

Related U.S. Application Data
(60) Provisional application No. 60/058,307, filed on Sep. 9, 1997.

(51) Int. Cl.[7] ..................... A61K 31/353; C07D 311/62
(52) U.S. Cl. ................. 514/456; 549/400; 549/415
(58) Field of Search ................. 514/456; 549/400, 549/415

(56) References Cited

U.S. PATENT DOCUMENTS

| | | |
|---|---|---|
| 4,083,779 A | 4/1978 | Combe et al. |
| 4,309,207 A | 1/1982 | Devlin |
| 4,652,448 A | 3/1987 | Sadowski |
| 4,698,360 A | 10/1987 | Masquelier |
| 4,775,477 A | 10/1988 | Stahl et al. |
| 4,857,327 A | 8/1989 | Virdalm |
| 5,128,100 A | 7/1992 | Hollis et al. |
| 5,200,186 A | 4/1993 | Gabetta et al. |
| 5,474,774 A | 12/1995 | Walker et al. |
| 5,494,661 A | 2/1996 | Tempesta |
| 5,525,341 A | 6/1996 | Walker et al. |
| 5,607,965 A | 3/1997 | Kondo et al. |
| 5,646,178 A | 7/1997 | Walker et al. |
| 5,650,432 A | 7/1997 | Walker et al. |
| 5,670,538 A | 9/1997 | Franchimont et al. |
| 5,683,678 A | 11/1997 | Heckert et al. |
| 5,773,262 A | 6/1998 | Ariga et al. |
| 5,840,322 A | 11/1998 | Weiss et al. |
| 5,912,363 A | 6/1999 | Nafisi-Movaghar et al. |

FOREIGN PATENT DOCUMENTS

| | | |
|---|---|---|
| WO | WO 95/26197 | 10/1995 |
| WO | WO 96/28135 | 9/1996 |
| WO | WO 96/30033 | 10/1996 |

OTHER PUBLICATIONS

Marwan and Nagel (1986) J. Food Sci. 51(4):1009–1013. "Microbial inhibitors of cranberries."
Marwan and Nagel (1986) J. Food Sci. 51(4):1069–1070. "Characterization of cranberry banzoates and their antimicrobial properties."
Morimoto et al. (1988) Chem. Pharm. Bull. 36(1):33–38. "Tannins and related compounds. Isolation and characterization of proanthocyanidins with a doubly–linked unit from Vaccinium vitis–idaea L."
Ofek et al. (1991) N. Engl. J. Med. 324:1599. "Anti–Escherichia coli adhesion activity of cranberry and blueberry juices."
Porter, Structure and Chemical Properties of the Condensed Tannins, in Plant Polyphenols 245–258 (Hemingway & Laks eds., 1992).
Porter, Flavans and Proanthocyanidins, in Flavonoids: Advances in Research Since 1986, 23–55 (Harborne ed., 1994).
Scalbert (1991) Phytochemistry 30(12):3875–3883. "Antimicrobial properties of tannins."
Schilling et al. (1973) Liebigs Ann. Chem. 9:1471–1475. "$^{13}$C–NMR–Spektroskopische Konstitutionsermittlung der $C_{30}H_{24}O_{12}$–Procyanidine."
Schmidt and Sobota (1988) Microbios. 55:173–181. "An examination of the anti–adherence activity of cranberry juice on urinary and nonurinary bacterial isolates."
Sobota (1984) J. Urol. 131:1013–1016. "Inhibition of bacterial adherence by cranberry juice: Potential use for the treatment of urinary tract infections."
Swain and Hillis (1959) J. Sci. Food Agric. 10:63–68. "The phenolic constituents of Prunus domestica,".
Thompson et al. (1972) J. Chem. Soc., Perkin Trans. I:1387–1399. "Plant Proanthocyanidins: Part 1. Introduction: Isolation, structure, and distribution in nature of plant procyanidins."
Wang et al. (1987) J. Food Sci. 43(5):1402–1404. "Isolation and Characterization of Polyphenolic compounds in cranberries."
Wang et al. (1996) Phytochemistry 43(2):359–365. "Differential inhibition of eukaryote protein kinases by condensed tannins."
Weinges (1971) Acta Phys. Chim. Debrecina 17:249–264. "Konstitution, entstehung und bedeutung der dimeren procyanidine."
Williams et al. (1983) Phytochemistry 22(2):569–572. "Molecular weight profiles of proanthocyanidin polymers."

(List continued on next page.)

Primary Examiner—Taofiq Solola
(74) Attorney, Agent, or Firm—Hale and Dorr LLP

(57) ABSTRACT

The present invention is directed to isolation and identification of plant proanthocyanidin extracts and particular proanthocyanidin compounds for prevention and treatment of urinary tract infections caused by P-type Escherichia coli. These extracts can be obtained from any proanthocyanidin-containing plants, including plants of the families Ericaceae, Rosaceae, Pinaceae, Vitaceae and the like. Preferably the extracts are from cranberry plants (especially, Vaccinium macrocarpon) and other plants, particularly fruit and berry plants from the Vaccinium spp. The extracts and compounds are also provided as pharmaceutical compositions, food additives and food compositions, especially beverages, ground meat preparations and cranberry-containing food products. The invention also relates to methods of reducing pathogenicity of P-type E. coli in the digestive tracts of cattle and reducing P-type E. coli contamination in ground meat as well as methods of detecting P-type bacteria.

12 Claims, 11 Drawing Sheets

OTHER PUBLICATIONS

Zafriri et al. (1989) Antimicrobial Agents and Chemotherapy 1:92–98. "Inhibitory activity of cranberry juice on adherence of Type 1 and Type P fimbriated *Escherichia coli* to eucaryotic cells."

Ahuja et al. (1989) J. Urol. 159:559–562. "Loss of fimbrial adhesion with the addition of*Vaccinium macrocarpon* to the growth medium of P–fimbriated *Escherichia coli*."

Avorn et al. (1994) JAMA 271(10):751–754. "Reduction of bacteriuria and pyuria after ingestion of cranberry juice."

Avorn (1996) Adv. Med. Biol. 408:185–186. "The effect of cranberry juice on the presence of bacteria and white blood cells in the urine of elderly women: What is the role of bacterial adhesion?"

Bomser et al. (1996) Planta Medica 62(3):212–216. "In vitro anticancer activity of fruit extracts for Vaccinium species."

Brantner and Grein (1994) J. Ethnopharmacol. 44(1):35–40. "Antibacterial activity of plant extracts used externally in traditional medicine."

Brenneisen and Steinegger (1981) Pharm. Acta Helv. 56(7):180–185. "Zur Analytik der Polyphenole der Früchte von *Vaccinium myrtillus L.* (Ericaceae)."

Chavan et al. (1979) J. Food Sci. 44(5):1319–1321. "Removal of tannins and improvement of in vitro protein digestibility of sorghum seeds by soaking in alkali."

Czochanska et al. (1979) J. Chem. Soc., Chem. Comm. 8:375–377. "Direct proof of a homogeneous polyflavan–3–ol structure for polymeric proanthocyanidins."

Czochanska et al. (1980) J. Chem. Soc., Perkin Trans: I:2278–2286. "Polymeric proanthocyanidins. Stereochemistry, structural units, and molecular weight."

Delcour et al. (1985) J. Chem. Soc., Perkin Trans. I:669–676. "Synthesis of condensed tannins. Part 13. The first 2,3–*trans*–3,4*cis*–procyanidins: sequence of units in a 'trimer' of mixed stereochemistry."

De Man et al. (1987) J. Clin. Microbiol. 25(2):401–406. "Receptor–specific agglutination tests for detection of bacteria that bind globoseries glycolipids."

Eerlingen and Delcour (1990) Chem. Mag. (Ghent) 16(2):16–19. "Gecondenseerde Looistoffen: Structuure en toepassingen."

Eshdat et al. (1978) Biochem. Biophys. Res. Commun. 85(4):1551–1559. "Isolation of mannose–specific lectin from *Escherichia coli* and its role in the adherence of bacteria to epithelial cells."

Fleet (1994) Nutr. Rev. 52(5):168–170. "New support for a folk remedy: Cranberry juice reduces bacteria and pyuria in elderly women."

Foo et al. (1982) Phytochemistry 21(4):933–935. "Proanthocyanidin polymers of fodder legunes."

Foo and Porter (1978) J. Chem. Soc., Perkin Trans. I:1186–1190. "Prodelphinidin polymers: Definition of structure units."

Foo and Porter (1981) J. Sci. Food Agric. 32(7?):711–716. "The structure of tannins of some edible fruits."

Freudenberg and Weinges (1965) Bull. Natl. Inst. Sci. India 31:24–27. "Condensed proanthocyanidins."

Hagerman (1987) J. Chem. Ecol. 14(2):453–461. "Extraction of tanning from fresh and preserved leaves."

Haslam, *Chemistry of Vegetable Tannins* (Academic Press 1966).

Jacques et al. (1973) J. Chem. Soc., Chem. Comm. 1:518–520. "Structure of the dimeric proanthocyanidin–A2 and its derivatives."

Jones et al. (1976) Phytochemistry 15:1407–1409. "The condensed Tannins of pasture legume species."

Kuzminski (1996) Nutr. Rev. 54(11,II,S):S87–S90. "Cranberry juice and urinary tract infections: Is there a beneficial relationship?"

Laks et al. (1987) J. Chem. Soc.,,Perkin Trans. I:1875–1881. "Condensed tannins. Base–catalysed reactions of polymeric procyanidins with phloroglucinal: Intramolecular rearrangements."

Lea, Flavor, Color, and Stability in Fruit Products: The Effect of Polyphenols, in Plant Polyphenols 827–847 (Hemingway & Laks eds., 1992).

Leibusor et al. (1996) J. Dent. Res. (IADR Abstracts) 75:1527. "Cranberry juice inhibits coaggregation of oral bacteria."

Madhavi et al. (1995) J. Food Sci. 60(2):351–355. "Expression of anthocyanins in callus cultrues of cranberry *Vaccinium macrocarpon*."

Magistretti et al. (1988) Arzneim.–Forsh./Drug Res. 38(5):686–690. "Autiulcer activity of an anthocyanidin from (*Vaccinium myrtillus AIT*)."

Where n= 4 or more

PLANT PROANTHOCYANIDIN EXTRACT EFFECTIVE AT INHIBITING ADHERENCE OF BACTERIA WITH P-TYPE FIMBRIAE TO SURFACES

This application is a continuation-in-part of provisional application U.S. Ser. No. 60/058,307, filed Sep. 9, 1997.

FIELD OF THE INVENTION

The present invention is directed to isolation and identification of plant proanthocyanidin extracts. These extracts can be obtained from any of a variety of proanthocyanidin-containing plants including members of the plant families Ericaceae, Rosaceae, Pinaceae and Vitaceae, and preferably are from cranberry plants (especially *Vaccinium macrocarpon*), other Vaccinium spp. and grapes (Vitus spp.) These extracts are useful for prevention and treatment of urinary tract infections caused by P-type fimbriated *Escherichia coli* as well as other uses. Extracts containing proanthocyanidins with A-type interflavanoind bonds have been found to have potent bioactivity for inhibiting adherence of P-type *E. coli*.

BACKGROUND OF THE INVENTION

Millions of women each year are diagnosed with cystitis (bladder infections) and pyelonephritis (kidney infections). Countless numbers of dogs and cats also suffer from chronic urinary infections and die from renal infections. *E. coli* bacteria is the most common pathogen associated with these infections, causing over 80% of urinary tract infections. Over 30% of women suffer recurrent infections within a 6 to 12-month period and are forced to resort to extended use of antibiotics to treat these infections. Recurrent use of antibiotics can lead to pathogen resistance and result in deleterious side effects and toxicity reactions. Consequently there exists a need for safe alternative medications (e.g., non-antibiotics) that can be used to prevent or treat urinary tract infections in both animals and humans.

Cranberry juice has been shown to reduce bacteriuria associated with urinary tract infections in humans (Avorn et al., 1994, J. Am. Med. Soc. 271:751–754). The effect appears to be due to the ability of certain cranberry compounds to inhibit adhesion of type 1 (implicated in bladder infections) and P-type (implicated in kidney infections) *E. coli* bacterial phenotypes to human bladder epithelial cells (Sobota, 1984, J. Urol. 131:1013–1016; Schmidt & Sobota, 1988, Microbios. 55:173–181; Zafriri et al., 1989, Antimicrob. Agents Chemo. 33:92–98). Zafriri et al. (1989) reported that fructose was responsible for the inhibition of type 1 *E. coli* to uroepithelial cells. Zafriri et al. also reported that cranberry juice contained a non-dialyzable substance (or substances) which inhibited binding of P-type *E. coli* but failed to define the chemical nature of this inhibitor. Cranberry juice has also been shown to cause immediate inhibition of agglutination as well as loss of fimbriae after long-term exposure of bacteria to the juice (Ahuja et al., 1998, J. Urol. 159:559–562).

A partially-purified anti-adherence activity from cranberry has also been described (U.S. Pat. Nos. 5,474,774; 5,525,341; and 5,646,178, all to Walker et al.). This activity was obtained using acidified alcohol as an extraction solvent with whole cranberry fruit followed by separation of the activity from monomer and dimer sugars by precipitation with a metal acetate or sulfate. Upon further manipulation, the reported activity consisted of a fraction enriched for polyphenol and flavonoid compounds that contained as much as 10% anthocyanins. The specificity of this anti-adherence activity for type 1 or P-type *E. coli* was not determined.

Walker et al. (WO 96/30033; and U.S. Pat. Nos. 5,646, 178 and 5,650,432) described a series of proanthocyanidin monomers, dimers, polymers, flavonoid derivatives thereof and related compounds purported to have the ability to interfere with bacterial adherence to a surface. The dimers and polymers of Walker were limited to compounds having B-type interflavanoid linkages. However, Walker failed to provide any experimental data correlating biological activity with a specifically-identified compound. The Walker method involved alkalinizing a plant material homogenate to a pH greater than 10, a treatment which causes degradation of proanthocyanidins, and precipitating the polyphenolic compounds (together with other materials) by addition of alcohol. This precipitate contained the proposed anti-adherence activity and was further fractionated to yield the purified active compound. Using this process with an aqueous solution of commercially-available Ocean Spray cranberry powder, Walker reported obtaining a single active compound and partially characterized the compound but failed to provide a complete (or any) chemical structure for this compound. Walker also failed to characterize the biological activity of this compound with respect to inhibition of adherence of type 1 or P-type *E. coli*. In fact, the Walker assay methods could not distinguish between these two biological activities.

Thus, prior to the present invention, there had been no identification of the class of bioactive compounds that inhibit P-type *E. coli* from adhering to surfaces such as uroepithelial cells. In accordance with the invention, it has been discovered that extracted mixtures of proanthocyanidins and purified proanthocyanidins are the bioactive compounds present in cranberry and other plants that possess anti-adherence activity against P-type *E. coli*.

A large variety of plants are known to contain proanthocyanidins and methods for isolating small amounts of proanthocyanidins from several different plant species have been reported. Various purification methods for proanthocyanidins from plant material have been described by Thompson et al. (1972, J. Chem. Soc., Perkins Trans. I. 11:1387); Jones et al. (1976, Phytochem. 15:1407–1409); Wang et al. (1978, J. Food Sci. 43:1402–1404); Czochanska et al. (1980, J. Chem. Soc., Perkin Trans. I:2278–2286); Foo & Porter (1981, J. Sci. Food Agric. 32:711–716); Marwan & Nagel (1986a, J. Food Sci. 51:1009–1013); Marwan & Nagel (1986b, J. Food Sci. 51:1069–1070); Morimoto et al. (1988, Chem. Pharm. Bull. 36:33–38); Devlin, U.S. Pat. No. 4,309, 207; and Bomser et al. (1996, Planta Med. 62:212–216).

Accordingly, the present invention identifies proanthocyanidins as the compounds that mediate inhibition of adherence of P-type *E. coli* to cellular surfaces and further provides an improved method of obtaining substantially pure mixtures of proanthocyanidins as well as individual proanthocyanidin compounds from the plant material of cranberries and other plants known to contain proanthocyanidins. These proanthocyanidin mixtures and individual proanthocyanidin compounds are thus useful in the prevention and/or therapeutic treatment of urinary tract infections, particularly those infections mediated by P-type *E. coli* or other microorganisms that contain structurally-related fimbriae or molecules involved in microbial adherence.

There also exists a need for an inexpensive and rapid test to identify the type of urinary tract infection that a person has contracted. Current clinical diagnosis is based on counting the number of bacteria present in a patient's urine without attempting to distinguish the bacterial strain as type 1 *E. coli*, P-type *E. coli* or a mixture of both. Since kidney infections (associated more with P-type *E. coli*) are usually more serious than bladder infections (associated more with type 1 *E. coli*) and require different treatment regimes, having a test to distinguish between these phenotypic strain variations would be beneficial. Thus, an inexpensive, rapid diagnostic kit to diagnose P-type infection would allow patients to receive the proper treatment in a more timely manner and avoid the use of ineffective medications. Accordingly, the invention also addresses this problem by providing proanthocyanidin mixtures which specifically bind to P-type *E. coli* as receptor analogs or prevent P-type fimbrial induction for assay kits designed to aid in the clinical diagnosis of pyelonephritis-type infections.

SUMMARY OF THE INVENTION

The present invention is directed to proanthocyanidin extracts substantially free of anthocyanins and flavonols. These extracts are also shown to be free of hydrolyzable tannins, alkaloids, lipids, carbohydrates, simple sugars, protein and amino acids, alcohols and organic acids by chemical reagent testing. These proanthocyanidins extracts are capable of inhibiting agglutination reactions of P-type *E. coli* but not type 1 *E. coli*. In particular, those extracts containing proanthocyanidins with at least one A-type interflavanoid bond have been found to be more bioactive in agglutination reactions than proanthocyanidins linked only by B-type interflavanoid bonds.

The invention also provides a method of obtaining these proanthocyanidin extracts from the plant material from any of a variety of proanthocyanidin-containing plants. The preferred plants are in the Ericaceae, Rosaceae, Pinaceae and Vitaceae families, particularly the Vaccinium species of the Ericaceae family, and the Vitis species of the Vitaceae family, and most preferably from cranberries (especially from *V. macrocarpon*). The method is applicable for extracting the proanthocyanidins from any portion of the plant including leaves, ripe fruit and unripe fruit. The method of the invention causes substantially less oxidative damage and/or atructural degradation to the proanthocyanidins, i.e., is less harsh, and provides improved yields of purified proanthocyanidins relative to known methods.

More particularly, the method of the invention is directed to preparing a proanthocyanidin extract from a plant by (a) homogenizing plant material in an aqueous extraction solvent comprising at least about 10% water but no more than about 30% water, about 10% to about 70% acetone, about 5% to about 60% methanol and about 0.05% to about 1% ascorbic acid; and subjecting that extract to further purification to allow recovery of a substantially purified proanthocyanidin extract which is capable of inhibiting agglutination of P-type *E. coli* but incapable of inhibiting agglutination of type 1 *E. coli*.

Hence, a preferred embodiment of the invention relates to a method of preparing a proanthocyanidin extract from a Vaccinium species which comprises:

(a) homogenizing Vaccinium plant material in an aqueous extraction solvent comprising at least about 10% water but no more than about 30% water, about 10% to about 70% acetone, about 5% to about 60% methanol and about 0.05% to about 1% ascorbic acid to prepare a first extract;

(b) clarifying and obtaining the supernatant from the first extract;

(c) removing the solvent from the supernatant and resuspending the residue in distilled water;

(d) subjecting the resuspended residue solution to further purification by either (i) applying the residue solution to reverse-phase lipophilic chromatography material equilibrated in distilled water and successively washing the lipophilic chromatography material with distilled water to remove sugars, with about 15% aqueous methanol to remove acids and with about 100% acidified methanol to elute polyphenolic compounds, and removing solvent from the polyphenolic fraction to obtain a first dried polyphenolic fraction, or (ii) extracting the residue solution with a non-polar extraction solvent, recovering the aqueous phase and removing solvent therefrom to obtain a second dried fraction;

(e) suspending the first or second dried fraction in about 50% aqueous ethanol, applying that solution to mixed hydrophilic-lipophilic chromatography material equilibrated in about 50% aqueous ethanol, and washing the mixed hydrophilic-lipophilic chromatography material with about 50% aqueous ethanol to remove non-proanthocyanidin polyphenolic compounds; and (f) eluting the mixed hydrophilic-lipophilic chromatography material with about 70% aqueous acetone to obtain the proanthocyanidin extract. This proanthocyanidin extract inhibits the agglutination of P-type *E. coli* but does not inhibit agglutination of type 1 *E. coli*.

The proanthocyanidin extract can be further fractionated using HPLC or other techniques to identify and characterize specific proanthocyanidin compounds that have anti-adherence activity against P-type *E. coli* or other microorganisms.

Such compounds include proanthocyanidin compounds having an average of at least four to about seven epicatechin flavanoid units, wherein at least two of the units are linked together by an A-type double interflavanoid bond between C4 and C8 and between C2 and the oxygen of C7 and the remaining units are linked to each other by a B-type interflavanoid bond between C4 and C8 or between C4 and C6.

Another aspect of the invention relates to methods of preventing or treating urogenital infections in a mammal by administering a proanthocyanidin composition comprising the proanthocyanidin extract, a proanthocyanidin compound, a proanthocyanidin polymer or a mixture thereof, to the mammal in an amount and for a time sufficient to prevent, reduce or eliminate the symptoms associated with such infections and thereby lead to an amelioration or curing of the infection. Preferably the mammal undergoing treatment is a human, but the method is also applicable to animals, especially domesticated animals such as cats and dogs and livestock animals such as cattle.

As used herein a "proanthocyanidin composition" comprises a proanthocyanidin extract of the invention, a proanthocyanidin compound of the invention, a proanthocyanidin polymer or a mixture thereof. The proanthocyanidin composition can be provided as a pharmaceutical composition, e.g., in pill form, as a food additive, e.g. for a beverage, or as a food composition. When a proanthocyanidin composition of the invention is provided in a cranberry juice beverage, the proanthocyanidins can enhance the cranberry juice's known benefits for preventing and treating urinary tract infections.

Hence, pharmaceutical compositions are provided which comprise a proanthocyanidin composition, including pharmaceutically-acceptable salts of any of the proanthocyanidin compounds or polymers, with a pharmaceutically acceptable carrier. In some instances, it may be preferable to provide the therapeutic dosage in the form of a food additive in a beverage such as a cranberry juice-based beverage containing additional proanthocyanidins. The invention also provides food compositions comprising a proanthocyanidin composition, including pharmaceutically-acceptable salts of the compounds or polymers, mixed with a consumable carrier. Consumable carriers include, but are not limited to, livestock feed, domestic animal feed and consumable food products, especially a cranberry-containing food products. These food compositions are also useful to prevent or treat urinary tract infections.

In another embodiment, the proanthocyanidin composition of the invention can be used to reduce the pathogenesis of P-type *E. coli* found in the digestive tracts of cattle. Such a method may be useful in decreasing contamination of ground meat prepared from such cattle.

Yet another aspect of the invention relates to a method of detecting P-type *E. coli* in a body fluid, especially in urine, and use of that method in diagnosis of pyelonephritis or other urinary tract infection associated with P-type *E. coli*. A kit for detecting P-type *E. coli* is also provided.

A still further aspect of the invention is directed to methods of reducing the incidence of infection after surgery, treating topical wounds and acne, and preventing or eliminating oral infections using the proanthocyanidin composition of the invention.

Further still, the proanthocyanidin composition of the invention can also be used as a food additive to confer protection against *E. coli* present in certain food products such as ground meat and unpasteurized juices, or as a feed additive to reduce the pathogenesis of P-type *E. coli* found in the digestive tracts of animals, especially cattle destined for slaughter. When used as a food additive for ground meat, it is preferable to add the proanthocyanidin composition to the meat preparations before or during grinding thereof.

BRIEF DESCRIPTION OF THE DRAWINGS

FIG. 3C shows the signal from 60–210 ppm and FIG. 3D shows the signal from 0–110 ppm. The chemical shifts of the peaks are as indicated.

FIG. 4C shows the signal from 80–210 ppm and FIG. 4D shows the signal from 0–110 ppm. The chemical shifts of the peaks are as indicated.

DETAILED DESCRIPTION OF THE INVENTION

Figure 1:
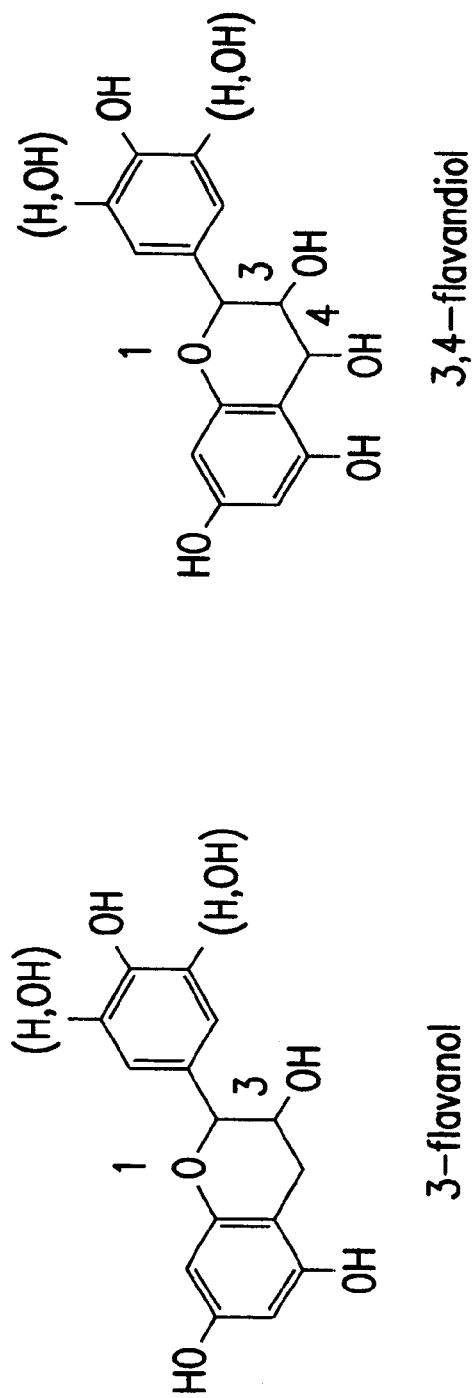
FIG. 1 depicts the chemical structures of 3-flavanol, 3,4-flavandiol and (–)-epicatechin.
Figure 1:
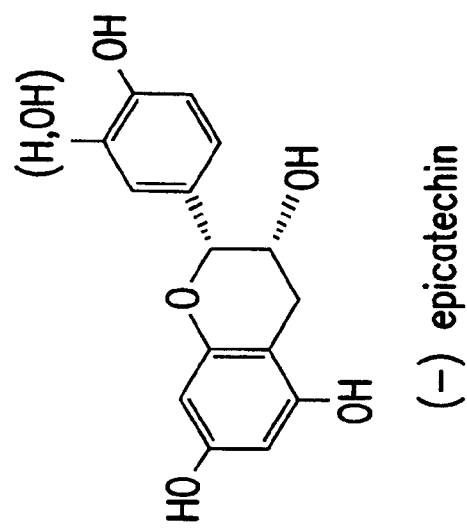

Proanthocyanidins are polyphenolic molecules found in fruits, berries and other plant material. These molecules belong to the flavanoid family of compounds. The flavanoid polyphenolics include the catechins, anthocyanins, and proanthocyanidins. Proanthocyanidins are also known as proanthocyanins, leucoanthocyanins, anthocyanogens or procyanidins; these terms can be used interchangeably. For general reviews see, Porter, "Flavans and Proanthocyanidins" in *The Flavonoids: Advances in Research Since* 1986 (Harborne, ed.) Chapman and Hall, London, 1993, pp.23–55; Haslam, *Chemistry of Vegetable Tannins*, Academic Press, New York, N.Y., 1966; or Singleton and Esau, *Phenolic substances in Grapes and Wine, and Their Significance* (1969). Proanthocyanidins are oligomers of 3-flavanols and/or 3,4-flavandiols which dehydrate upon acid treatment to yield anthocyanins. Proanthocyanidins are also referred to as anthocyanogens in the older literature, i.e. anthocyanin-formers. The 3-flavanol monomers of catechin and epicatechin are commonly found in proanthocyanidins. The structures of 3-flavanol, 3,4-flavandiol and epicatechin are provided in FIG. 1.

It is believed that the proanthocyanidins are similar in structure to the bacterial-binding receptors found on the surface of bladder or kidney cells. These compounds may act, not by killing the bacteria directly, but rather by binding bacterial fimbriae and thereby preventing adherence of the bacteria to bladder or kidney cell surface receptors. Alternatively, the proanthocyanidins may inhibit biosynthesis of the bacterial fimbriae, without which adherence cannot occur. No matter the mechanism, if the bacteria cannot bind to the cells, they cannot multiply, and these are two steps apparently necessary to cause a urinary tract infection. The bacteria are thus carried harmlessly out of the body in the urine stream. This anti-adherence property is advantageous since it eliminates the selective pressure to develop antibiotic resistance that can occur during multiplication of bacteria in the presence of antibiotics.

In one embodiment, this invention is directed to a substantially purified proanthocyanidin extract from a plant, preferably a plant from the family Ericaceae, Rosaceae, Pinaceae or Vitaceae in which the extract is capable of inhibiting agglutination of P-type *E. coli* but not inhibiting agglutination of type 1 *E. coli*. More preferably the extract is prepared from a Vaccinium spp. or a Vitis spp. and most preferably from *V. macrocarpon* in accordance with the methods described herein. Inhibition of agglutination can be measured by known agglutination assay methods or know methods of measuring bacterial adherence to a surface. These assay methods can also be used to follow purification of the proanthocyanidin extract from plant homogenate material.

For example, A-positive (A+) blood type human red blood cells (HRBC) specifically bind P-type fimbriated *E. coli* and the extract of the invention will prevent (i.e., inhibit) agglutination of the A+HRBC in the presence of P-type bacteria. There are also synthetic P-type receptor analogs known in the art which can be used to coat solid substrates, e.g., latex beads, and then used to assay the extract for its ability to inhibit agglutination of P-type bacteria. Agglutination assays specific for type 1 fimbriated *E. coli* are also known and are similar to those described above, except that the HRBC can be replaced by guinea pig red blood cells (GPRBC) or by yeast cells, e.g., *Saccharomyces cerevisiae* and the agglutination is done in the presence of type 1-fimbriated bacteria. Details for performing these assays are provided in the Examples.

Moreover, the extract of the invention is substantially free of anthocyanins, flavonols, hydrolyzable tannins, alkaloids, lipids, carbohydrates, simple sugars, protein and amino acids, alcohols and organic acids. The presence or absence of these compounds can be determined by standard chemical testing, measures of purity or other conventional means known in the art. In one method, the extract (or other fraction to be tested) can be spotted on thin-layer chromatography (TLC) plates, developed in an appropriate solvent system and then treated with a test reagent for a specific class of compounds like tannins, alkaloids, lipids and the like to determine whether those compounds were present in the test sample. A variety of useful TLC tests are described in Example 2. Other chemical or purity determining methods include colorimetric detection of anthocyanidin formation, HPLC purification and $^1$H- and $^{13}$C-NMR spectroscopic identification. These methods are known and some specific examples thereof are also set forth in Example 2.

A proanthocyanidin extract prepared from *V. macrocarpon* in accordance with the methods of this invention comprises proanthocyanidin compounds consisting of an average of at least four to about seven epicatechin flavanoid units, wherein at least two units are linked together by at least one A-type interflavanoid linkage and the remaining units are B-type interflavanoid bonds. In a preferred embodiment, these proanthocyanidin compounds consist of an average of from about four to six epicatechin flavanoid units.

To simplify reference to specific carbons in the flavanol rings of the proanthocyanidins, carbons at specific positions are referred to by Cn, where the n represents the position number of the carbon in the standard flavanol ring numbering system. Thus the carbon at the eight position of the ring is designated as C8, the carbon at the four position of the ring is designated as C4, etc. Unless specifically stated otherwise, linkages between ring positions can occur in either the α or β anomeric orientation.

An A-type interflavanoid linkage is one which results when the flavanoid units are joined by two bonds, with one bond occurring between C4 of the "upper or first" unit and C8 of the "lower or second" unit and the other bond occurring between C2 of the upper unit and the oxygen attached to the C7 of the lower unit. This linkage leads to the formation of an additional 6-membered ring. A B-type interflavanoid bond (or linkage) is one which results when the flavanoid units are joined by a single bond. That bond occurs between either the upper unit C4 and the lower unit C8 or between the upper unit C4 and the lower unit C6.

In addition to obtaining proanthocyanidin compounds via the extraction procedure and purification procedures of the invention, the present invention also embraces proanthocyanidin compounds prepared by chemical synthesis. Methods of synthesizing proanthocyanidins are known in the art, for example, Delcour et at., 1985, J. Chem. Soc. Perkin Trans. I:669–676.

Another aspect of the invention is directed to a method of preparing a proanthocyanidin extract from a plant which comprises (a) homogenizing plant material in an aqueous extraction solvent comprising at least about 10% water but no more than about 30% water, about 10% to about 70% acetone, about 5% to about 60% methanol and about 0.05% to about 1% ascorbic acid to prepare a first extract; (b) subjecting that first extract to further purification steps; and (c) recovering therefrom a substantially purified proanthocyanidin extract, which is capable of inhibiting agglutination of P-type *E. coli* but not type 1 *E. coli*. The method is applicable to plant material from any proanthocyanidin-containing plant and is preferably used with Vaccinium spp., especially *V. macrocarpon* or other cranberry species. The preferred aqueous extraction solvent comprises about 40% acetone, about 40% methanol and about 0.1% ascorbic acid.

Many plants are known to contain proanthocyanidins, and any such plants can be employed in the method of the invention. Proanthocyanidin-containing plants are members of the Coniferiae class including plants from the order Coniferales and particularly from the family Pinaceae (including pines); members of the family Filices (including palms); monocot plants form the order Arecales, including members of the families Pandanales, Arales, Najadales, Restionales, Poales (including grains such as sorghum, barley and others), Juncalaes, Cyperales (including cypress), Typhales, Zingiverales, and Liliales (including lilies); dicot plants from the orders Laurales (including laurel, cinnamon), Fagales (including oak), Casuarinales, Dilleniales, Malviales (including cotton), Salicales, Ericales (including cranberries, blueberries, rhododendron), Ebenales, Rosales (including roses, blackberries and other related berries, apples, peaches, plums), Fabales (including legumes, wysteria), Myrtales, Proteales, Rhamanales (including grapes) and Sapindales. The preferred plants are the dicots Ericaceae, which includes the Vaccinium spp., Rosaceae and Vitaceae, which includes the Vitis spp.; and the conifers of the Pinaceae family. The Vaccinium spp. include, but are not limited to, plants with cranberry-type berries such as *V.macrocarpon* (cranberry), *V. vitis-idaea* (mountain cranberry, cow berry, lingonberry) and *V. oxycoccus* (European cranberry); and plants with blueberry fruit such as *V. augustifolium* (low sweet blueberry), *V. ashei* (Rabbiteye blueberry), *V. corymbosum* (high bush blueberry), *V. lamarckii* (early sweet blueberry) and *V. myrtillus* (bilberry, European blueberry). The Vitis spp. include, but are not limited to, *V. labrusca* (Fox grape), *V. rotunddifolia* (muscadine, scuppenong), *V. vinifera* (European grape) and all interspecifc hybrids with other Vitis species.

In one preferred purification scheme, a proanthocyanidin extract of the invention is prepared by homogenizing plant material from a plant which contains proanthocyanidins with an aqueous solution of 40% acetone, 40% methanol and 0.1% ascorbic acid. After homogenization, the extract is clarified by filtration or centrifugation, the pulp is discarded and the supernatant designated as Fraction 1. The solvents are then removed from the supernatant by evaporation and the residue is resuspended in distilled water and subjected to further purification by (1) fractionation on a reverse-phase lipophilic column, such as a C-18 column or other comparable column, equilibrated in distilled water and eluted with successive washes of water (yielding Fraction 2), 15% aqueous methanol (yielding Fraction 3), or acidified 100% methanol (yielding Fraction 4 which can be evaporated to dryness before further purification) or (2) by extraction with a non-polar solvent such as petroleum ether, hexane and the like. The non-polar phase, Fraction 5, is discarded and the aqueous phase, Fraction 6, can also be evaporated to dryness before further purification.

The next step in the purification process is to resuspend Fraction 4 or 6 in 50% aqueous ethanol and apply that solution to a mixed lipophilic-hydrophilic column such as Sephadex™ LH-20 or LH-60 (Pharmacia Biotech) equilibrated in 50% ethanol. Other separation media such as MCI gel (Mitsubishi Chemical) or TSK gel (Tosohaus) can be substituted. The column is washed in the same solvent system until the non-proanthocyanidin polyphenolic compounds are removed (Fraction 7). Hence complete washing can be monitored by removal of the red color attributed to the anthocyanin pigment. A purified mixture of proanthocyanidins is then obtained by eluting the column with 70% aqueous acetone. The resulting mixture (Fraction 8) can be lyophilized and stored at 4° C. in the dark to minimize oxidation.

As an alternative, Fractions 4 or 6 can be further separated into low and higher molecular weight proanthocyanidins mixtures by liquid-liquid extraction with ethyl acetate and water prior to further purification. In this case, Fractions 4 or 6 are resuspended in water and extracted four times with an equal volume of ethyl acetate. The ethyl acetate phases are combined and contain the lower molecular weight proanthocyanidins, whereas the aqueous phase contains the higher molecular weight proanthocyanidins. Both post-extraction phases are evaporated to dryness to remove solvent and then further purified on Sephadex LH-20 as described above. The purified material obtained from fractionating the water-soluble phase on the Sephadex LH-20 column is designated as Fraction 8a. The purifed material obtained from fractionating the combined ethyl acetate-soluble phases on the Sephadex LH-20 column is designated as Fraction 8b.

As used herein, an aqueous alcohol solution means a solution of water and alcohol having the specified percentage of alcohol. For example, 15% aqueous methanol means a solution having 15 parts methanol and 85 parts water and 50% aqueous ethanol means a solution having 50 parts ethanol and 50 parts water. Similarly, an aqueous acetone solution means a solution of water and acetone having the specified percentage of acetone. Further, 100% acidified methanol means methanol containing from about 0.005% to about 0.1% acid. The 100% methanol solution of the Examples is methanol and 0.01% ascorbic acid.

In the purification schemes described above, the fractionation steps employ column chromatography. However, the skilled artisan will recognize that the purification steps can also be carried out in batch with straightforward modifications.

In accordance with the invention, the plant material can be from any part of the plant and preferably is from a part of the plant rich in proanthocyanidins. For example, plant material includes leaves, fruit (both mature or ripe fruit, and immature or unripe fruit), stems, seeds, bark and roots, and can be used for preparation of the proanthocyanidin extract. In the case of Vaccinium species, the plant material is preferably from leaves or fruit. For *V. macrocarpon*, leaves provide the richest source of proanthocyanidins. The mature fruit from *V. macrocarpon* is red whereas the immature fruit is green.

The solution used to homogenize the plant material is important in obtaining high extraction yields of the proanthocyanidins. The preferred solution is an aqueous solution of 40% acetone, 40% methanol and 0.1% ascorbic acid. However, the amounts of each component in the extraction solvent range from 10% to about 70% for acetone, from about 5% to about 60% for methanol and from about 0.05% to about 1% ascorbic acid, provided that in all cases there is a minimum of at least about 10% water to a maximum of about 30% water. The ascorbic acid can also range from about 0.05% to about 0.2%.

Acetone is more effective than alcohols alone or aqueous alcohols for solubilizing and extracting proanthocyanidins from plant tissues (Hagerman, 1988, J. Chem. Ecol. 14 (2): 453–461). If extracting from leaf tissue, acetone inhibits the interaction between proanthocyanidins and proteins, preventing binding of the proanthocyanidins to leaf proteins during the homogenization process (Hagerman, 1988) and resulting in a higher yield of extracted proanthocyanidins. In addition, because skin waxes, proteins, and polysaccharides are relatively insoluble in acetone, these components tend to be left in the pulp. Methanol acts as a mild antioxidant and is important when extracting plant materials which contain large amounts of oxidase enzymes, such as found in fruit tissue. Water increases the polarity of the solvent mixture and enhances the solubility of the sample thereby increasing yields of the proanthocyanidins since these molecules are associated with the water-soluble components of the sample. Ascorbic acid acts as an antioxidant by reducing the quinones that are initially formed (Lea, 1992, Flavor, Color, and Stability in Fruit Products: The Effect of Polyphenols. In: Hemingway, R. W. (ed.) Plant Polyphenols. Plenum Press, New York) and also helps to maintain slightly acidic to neutral conditions during the homogenization and extraction process. Alkaline extraction conditions must be avoided since proanthocyanidin molecules are known to undergo base-catalyzed structural rearrangements at high pH that cannot be reversed upon exposure to acidic conditions (see, for example, Laks et al., 1987, J. Chem. Soc., Perkin Trans. I:1875). Upon testing, it was established that such structurally rearranged molecules (which are no longer proanthocyanidins) lose the ability to inhibit adherence of P-type *E. coli* bacteria to cellular surfaces.

In another embodiment the invention provides methods of preventing or treating urogenital infections in a mammal by administering a composition comprising the proanthocyanidin extract or proanthocyanidin compounds of the invention to the mammal in an amount and for a time sufficient to prevent, reduce or eliminate the symptoms associated with such infections and thereby lead to amelioration or curing of the infection. The composition can be a pharmaceutical composition or a food composition and is administered for a time and in an amount sufficient to reduce or eliminate the bacteria associated with urogenital infections and thereby ameliorate or cure the infection. The pharmaceutical composition can also be used to treat diarrhea. In connection with preventing infection or disease, to prevent an infection is not limited to nor necessarily means total prevention of the infection or disease but also includes uses which lead to action as a preventative for the disease or infection.

As used herein in connection with the various methods of use and in connection with the pharmaceutical and food compositions of the invention, the terms "proanthocyanidin compounds" and "proanthocyanidin polymers" of the proanthocyanidin compositions have the definitions of one or more of the following compounds or polymers.

There are several type of proanthocyanidin molecules known in the art and any of these are contemplated unless specified otherwise. The proanthocyanidins include, but are not limited to, procyanidins, prodelphinidins, propelargonidins and profisetinidins.

Hence proanthocyanidin compounds of the invention include proanthocyanidin compounds capable of inhibiting agglutination of P-type *E. coli* but incapable of inhibiting agglutination of type 1 *E. coli*, and which comprises two or more flavanoid monomer units wherein at least two of said units are linked together by an A-type interflavanoid linkage by bonds between C4 and C8 and between the C2 and the oxygen of C7 of the units and the remainder of any units are linked to each other by a B-type interflavanoid bond between C4 and C8 or between C4 and C6 of the units. These molecules can include from two to 10, 20, 30 or even more flavanoid and preferably have from 4 to 8 monomer units. The molecules have at least one A-type interflavanoid linkage, and molecules having a few such linkages, e.g., 2–3 A-type interflavanoid linkages per 10 monomer units, as well as molecules having all of the subunits joined by A-type interflavanoid linkages are contemplated. The flavanoid monomer units can include any of those typically found in proanthocyanidin molecules and are further defined hereinbelow.

The proanthocyanidin compounds of the invention further include proanthocyanidin compounds consisting of an average of from at least four to about seven epicatechin flavanoid units, and preferably from four to six units, wherein at least two of said units are linked together by an A-type interflavanoid linkage by bonds between C4 and C8 and between the C2 and the oxygen of C7 of the units and the remainder of the units are linked to each other by a B-type interflavanoid bond between C4 and C8 or between C4 and C6 of the units.

The proanthocyanidin polymers of the invention are those proanthocyanidin polymers capable of inhibiting agglutination of P-type E. coli but incapable of inhibiting agglutination of type 1 E. coli. The polymers include dimers, trimers, tetramers, pentamers, larger oligomers and long polymers of flavanoid monomer units so long as these polymers have the stated bioactivity.

Hence, the proanthocyanidin compounds and polymers of the invention are composed of flavanoid monomers, i.e., polyhydroxyflavan-3-ols, which include but are not limited to, catechin, epicatechin, gallocatechin, epigallocatechin and the like. These monomers can be chemically modified at positions not involved in formation of the interflavanoid linkages, including modifications of any hydroxy group not involved in polymerization, so long as the compounds are capable of inhibiting agglutination of P-type E. coli but incapable of inhibiting agglutination of type 1 E. coli. Such modifications include but are not limited to substitutions of the following groups at those positions: hydroxy, mercapto, halo, trifluoromethyl, alkyl, alkoxy, alkanoyl, haloalkyl, hydroxyalkyl, alkoxycarbonyl, alkylthio and alkanoyloxy. As used herein alkyl refers to alkyl chains having from one to six carbon atoms, in any straight or branched configuration. For example, such modifications can be found at the C3 and C5 positions, or the C6 or C8 position if those atoms are not involved in an interflavanoid linkage. Similarly the aryl ring at the C2 position of the flavanoid monomer can be aryl or heteroaryl, optionally substituted with any of the substituents set forth above. Aryl groups include but are not limited to phenyl, indenyl and naphthyl and the like. Heteroaryl groups include but are not limited to, furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl (or its N-oxide), thienyl, pyrimidinyl (or its N-oxide), indolyly, isoquinolyl (or its N-oxide) and quinolyl (or its N-oxide). Hence, all such modifications are included herein by reference to the terms "flavanoid monomer" or "flavanoid monomer unit".

Further, as used herein in connection with the various methods of using the proanthocyanidin extract of the invention and in connection with the pharmaceutical and food compositions described below, the term "proanthocyanidin extract" refers to one or more (a) substantially purified plant proanthocyanidin extracts capable of inhibiting agglutination of P-type E. coli but incapable of inhibiting agglutination of type 1 E. coli, including extracts prepared from plants in the families Ericaceae, Rosaceae, Pinaceae and Vitaceae, and preferably plants which are a Vaccinium or a Vitis species; and (b) a proanthocyanidin extract prepared by a method of the invention including extracts prepared from plants in the families Ericaceae, Rosaceae, Pinaceae and Vitaceae, and preferably plants which are a Vaccinium or a Vitis species.

Treatment in accordance with the invention renders bacteria non-pathogenic and unable to colonize the urinary tract. Thus, one measure of efficacy includes monitoring the reduction or elimination of urinary bacterial counts associated with such infections during or after the course of treatment. Prevention in accordance with the invention does not mean complete prevention of infection in any particular individual but rather means a statistical reduction in the incidence of urogenital infections in a population sample.

Pharmaceutical compositions comprise proanthocyanidin extracts or proanthocyanidin compounds together with a pharmaceutically acceptable carrier. The pharmaceutical composition can be provided, e.g., in tablet or liquid form, oral rinse, douche, topical formulation, toothpaste or as an additive for a beverage or other food item, especially as an additive for a cranberry juice beverage (or cranberry-juice containing beverage) to allow enhancement of the cranberry juice's known benefits for preventing and treating urinary tract infections.

Specific pharmaceutical compositions of the invention comprise a proanthocyanidin extract and a pharmaceutically-acceptable carrier, wherein the extract is capable of inhibiting agglutination of P-type E. coli and not capable of inhibiting agglutination of type 1 E. coli as well as any of the extracts prepared in accordance with a method of the invention. Another specific pharmaceutical composition of the invention comprises one or more proanthocyanidin compounds and a pharmaceutically-acceptable carrier, wherein the compounds are proanthocyanidin compounds consisting of an average of from at least four to about twelve epicatechin flavanoid units, wherein each unit is linked to the next by B-type interflavanoid bonds or proanthocyanidin oligomers consisting of an average of from at least four to about seven epicatechin flavanoid units, wherein at least two units are linked together by at least one A-type interflavanoid linkage and the remaining units are B-type interflavanoid bonds.

The proanthocyanidin compositions of the invention can be used directly as food additives or mixed with a consumable carrier to be used as a food additive or food composition. One food additive of the invention comprises a proanthocyanidin extract of a Vaccinium species and a consumable carrier, wherein the extract is capable of inhibiting agglutination of P-type E. coli and not capable of inhibiting agglutination of type 1 E. coli. Another food additive of the invention comprises one or more proanthocyanidin compounds and a consumable carrier, wherein the compounds are proanthocyanidin oligomers consisting of an average of from at least four to about seven epicatechin flavanoid units, wherein at least two units are linked together by at least one A-type interflavanoid linkage and the remaining units are B-type interflavanoid bonds.

The food compositions of the invention thus contain one of the proanthocyanidin compositions of the invention in admixture with livestock feed, domestic animal feed or with a consumable food product. Those food compositions which contain livestock feed are for cattle, pigs, turkeys, chickens and the like. Those food compositions which contain domestic animal feed are for dogs, cats, horses and the like. Those food compositions which contain a consumable food product are for mammals, preferably for humans and primates. The food compositions, especially beverages, can be used as therapeutics to prevent or treat urogenital infections. Alternatively, the food compositions can be general consumables, for example, ground meat or other meat product, beverages, especially juice beverages, whether or not pasteurized, grain products, fruit products and the like. Beverages which contain cranberry juice are preferred.

As used herein a consumable food product includes, but is not limited to, a cranberry-containing food product, a beverage, ground meat or any other edible product to which the proanthocyanidins can be added. Cranberry-containing food product include dried cranberries, sweetened and dried cranberries, flavored fruit pieces, cranberry sauces, cranberry jellies, cranberry relishes, cranberry juices or any other beverage or product containing cranberry juice and wine made from or with cranberries. Beverages include unpasteurized juice or pasteurized juice.

The preferred dosage range of proanthocyanidin composition is from about 1 mg to about 500 mg per day, preferably from about 10 to about 250 mg per day and more preferably from about 25 to 100 mg per day of extract, compound or polymer. Such dosages can be present in tablets or other pharmaceutical compositions as well as in the food compositions of the invention including beverages and other food items. If the beverage is cranberry juice, the dosage can be adjusted, if desired, to account for the proanthocyanidins already present in the juice. This adjustment can readily be made by one of skill in the art by determining the amount of proanthocyanidins present in the juice and making the appropriate compensation or desired supplementation. Similarly, if the patient is being treated with both cranberry juice and a proanthocyanidin supplement, then the dosage of proanthocyanidins needed to achieve an anti-adherence effect (or other effect such as a lessening of symptoms) could be reduced.

Use of a Vaccinium-derived (or other plant-derived) extract or pharmaceutical composition can be beneficial in places where cranberry juice is not available (third-world countries, etc.). Moreover, some people, especially the elderly, that suffer recurrent urinary tract infections cannot tolerate cranberry juice due to its high sugar and acid content and a proanthocyanidin-containing pharmaceutical composition would be an effective and desirable alternative.

Another aspect of the invention relates to methods of reducing P-type *E. coli* contamination in ground meat, preferably from cattle but also from pigs, chickens, turkeys or other livestock sources of ground meat. For example, raw meat can be obtained from a livestock animal and a food additive of the invention can be mixed with the raw meat before or during preparation of ground meat from the raw meat. Another way to reduce P-type *E. coli* contamination in ground meat comprises feeding a food composition of the invention to a livestock animal and preparing ground meat from that animal. The ground meat can be prepared solely from the meat of animals which have been fed a proanthocyanidin-containing food composition or can also contain meat from animals who did not feed on any proanthcyanidin-containing food compositions. In the latter case, the ground meat can be prepared, for example, using a proportion of raw meat from proanthocyanidin-fed animals sufficient to reduce the agglutination of P-type *E. coli* microorganisms in said ground meat relative to ground meat prepared only from raw meat of a similar livestock animal who has not been fed a proanthocyanidin-containing food composition of the invention.

The livestock animals may not need to be fed a proanthocyanidin-containing food composition during the entire duration of their lifetime. It may be beneficial and cost effective to feed the animals the food composition of the invention for a period prior to slaughter, e.g., for a few days or weeks or for as long as several months depending on the animal and age at which the animal is destined for slaughter.

In another embodiment, the present invention provides a method of inhibiting adherence of P-type *E. coli* to a surface which comprises contacting said bacteria with at least one proanthocyanidin composition, prior to or concurrently with contacting said bacteria with said surface. The surface can be any substance or material, synthetic or biological, where it is desired to prevent bacterial contamination, accumulation or infection. The surface can also be or constitute a biofilm. In a preferred embodiment the surface is a cellular surface such as an uroepithelial cell surface, cells exposed in a wound or on the skin or another surface such as teeth or a prosthetic device or implant or a biofilm on any of these objects. The proanthocyanidin composition used in this method can be any proanthocyanidin extract compound or polymer of the invention or a pharmaceutical product containing any of the foregoing.

The proanthocyanidin compositions of the invention can also be used for reducing or treating infection after surgery, treating topical wounds or acne, or preventing or eliminating oral infection by administering a pharmaceutical composition of the invention to a site of infection or potential infection in a patient. The pharmaceutical composition is administered to the patient in accordance with the treatment being rendered. For example, it can be applied to a surgical incision or other opening as a liquid, topical cream or by any other suitable delivery means. For topical wounds, the pharmaceutical composition can be a tropical cream, salve or spray. Oral infection can be treated by brushing with a toothpaste or by using a oral rinse or mouth wash formulated with proanthocyanidins in accordance with the invention.

Yet another aspect of the invention is directed to a method of detecting P-type reactive bacteria in a body fluid sample which comprises (a) contacting a body fluid sample with a P-type receptor specific assay reagent for a time and in an amount to allow binding of any P-type reactive bacteria which may be present in the sample to the reagent, wherein the reagent comprises a solid-phase substrate coated with one or more proanthocyanidin compositions of the invention; and (b) determining whether P-type reactive bacteria are present in said sample by assessing the degree of agglutination in said sample. The presence of P-type reactive bacteria, especially P-type *E. coli*, are present if agglutination occurs in the sample. Various modifications of the assay are contemplated including sandwich type assays and inhibition of agglutination assays.

Another embodiment of the invention provides a kit for use in detecting P-type reactive bacteria in a body fluid sample. The compartmentalized kit comprises a container adapted to contain a P-type receptor specific assay reagent which comprises a solid-phase substrate coated with one or more proanthocyanidin compositions of the invention. The kit can also contain diluent for the sample or the reagent. Further, the kit may be adapted, if desired, for conducting the assay directly in the container containing the reagent. Alternatively, the kit can contain a container adapted for conducting the assay, and especially for multiple serial dilutions of the sample or reagent as appropriate.

It is to be understood and expected that variations in the principles of invention herein disclosed in an exemplary embodiment may be made by one skilled in the art and it is intended that such modifications, changes, and substitutions are to be included within the scope of the present invention.

EXAMPLE 1

Preparation of Proanthocyanidin Extract

Leaves or fruit (red—mature and green—immature) (10 g fresh weight) of the plant *Vaccinium macrocarpon*

(cranberry) were washed, dried, and homogenized with 60 mL of extraction solvent (40% acetone, 40% methanol, 20% water, 0.1% ascorbic acid) in a blender for 10 min. The homogenized slurry was forced through 8 layers of cheesecloth, the pulp discarded, and the crude extract filtered or centrifuged at 5,000 rpm for 15 minutes to remove insoluble particulate matter. The clarified supernatant, designated as Fraction 1, was evaporated to dryness under reduced pressure to remove solvents and was resuspended in 17 mL distilled water. Lipids, waxes, sugars, and acids were removed from Fraction 1 by application of the fraction to a reverse-phase lipophilic column (C-18) that had been preconditioned with 1 column volume of methanol followed by 1 column volume of water. The column was successively washed with the indicated solvents as follows: Sugars were removed by washing with 2 column volumes of distilled water to produce Fraction 2. Acids were removed by washing with 2 column volumes of 15% aqueous methanol to produce Fraction 3. The polyphenolic compounds were completely eluted with 3 column volumes of 100% methanol acidified with 1% acetic acid to produce Fraction 4. Fraction 4 was evaporated to dryness before further purification.

As an alternative, the lipids and skin waxes present in Fraction 1 were removed by extracting Fraction 1 three times with an equal volume of petroleum ether. The petroleum ether-soluble phase, designated as Fraction 5, was discarded, and the aqueous phase, designated as Fraction 6, containing sugars, acids, and polyphenolic material was evaporated to dryness to remove all traces of solvent; the remaining sugars and acids were removed in subsequent steps.

For those samples analyzed by NMR (see Example 2, section D), Fraction 6 was subjected to an additional extraction step prior to further purification. To carry out this extraction, the aqueous phase designated as Fraction 6 was not evaporated to dryness but rather its volume was reduced and the resultant solution was extracted four times with an equal volume of ethyl acetate. The water-soluble fraction was reduced in volume and subjected to further purification on an Sephadex LH-20 column as described below. This purified preparation is designated as 8a and contains the water-soluble proanthocyanidins. The ethyl-acetate soluble fractions were combined, evaporated to dryness and further purified on a Sephadex LH-20 column as described below. This purified preparation is designated as 8b and contains ethyl acetate-soluble proanthocyanidins.

To separate the proanthocyanidins in Fraction 4 or 6 from other polyphenolic compounds, such as anthocyanins and flavonols, the dried fraction was resuspended in a minimum volume of 50% aqueous ethanol and applied to a glass column containing hydroxypropylated cross-linked dextran beads (Sephadex LH-20, Pharmacia Biotech) that had been equilibrated overnight in 50% aqueous ethanol. The column was washed with up to 10 column volumes of 50% aqueous ethanol or until all red color had been removed. This wash eluate, designated as Fraction 7, was composed of non-proanthocyanidin polyphenolic compounds (flavonols, anthocyanin pigments). When Fraction 6 was applied to the LH-20 column, the eluate also included any sugars and acids remaining from solvent partitioning. The proanthocyanidins, designated as Fraction 8, were then eluted from the column with up to 8 column volumes of 70% aqueous acetone, freeze-dried and stored in the dark at 4° C. to minimize oxidation. The freeze-dried material was weighed and the mg of proanthocyanidins (dry weight) per g fresh weight of unfractionated extract was calculated to determine the relative concentration of proanthocyanidins extracted from cranberry leaves and fruit (ripe and unripe) (Table 1).

TABLE 1

Proanthocyanidin Concentration in Cranberry Organs

| Source | Concentration of Proanthocyanidin Extract (mg/g)[a] |
|---|---|
| Leaves | 21.16 |
| Fruit (unripe) | 12.14 |
| Fruit (ripe) | 10.72 |

[a]Extract from Fraction 8; mg dry weight proanthocyanidin/g fresh weight source.

EXAMPLE 2

Composition of Proanthocyanidin Extract

A. Thin Layer Chromatography

Chemical testing was undertaken to demonstrate that Fraction 8 contained purified proanthocyanidins and was free from other constituents. Thin layer chromatography (TLC) was performed on precoated silica gel plates with a fluorescence indicator (Fisher Scientific). Fraction 8 from ripe fruit was spotted (+μl) onto TLC plates and developed with benzene-ethyl formate-formic acid (2:7:1) to determine whether a particular class of compounds was present. Each TLC plate was sprayed and/or treated with the chemical reagents for the indicated compounds as described below. After treatment, the TLC plates were examined and noted for development of spots and the color of those spots. The results are shown in Table 2 and demonstrate that the extracts are substantially pure proanthocyanidins.

The chemical reagent tests for specific compounds and expected results were as follows:

Tannins (general): A solution of 1% ferric chloride in 0.5 N HCl was sprayed on the TLC plate. Tannins yield a green-brown spot.

Procyanidins: A solution of 1% ethanolic vanillin and a solution of methanol:HCl (8:2, v/v) were successively sprayed on the TLC plate. A bright red spot indicates presence of procyanidins.

Hydrolyzable tannins: The TLC plate was sprayed with a saturated aqueous solution of potassium iodate. The galloyl esters produce a red to pink spot whereas gallic acid produces an orange-red spot.

Alkaloids: A mixture of 5% $I_2$ in 10% KI solution was made and then 2 parts of solution were mixed with 3 parts water and 5 parts 2 N acetic acid before spraying the TLC plate. Appearance of a spot(s) indicates that alkaloids are present.

Carbohydrates: A solution of 3% anthrone in boiling glacial acetic acid was sprayed on the TLC plate followed by a spray of ethanol:phosphoric acid:water (20:3:1, v/v). The plate was heated 5 min. at 110° F. Ketoses and oligosaccharides produce a yellow spot.

Simple sugars: The spray consisted of 1.23 g p-anisidine and 1.66 g phthalic acid dissolved in 100 mL methanol. Hexose sugars yield a green spot whereas pentose sugars yield a red-violet spot.

Protein/amino acids: A solution of 2% vanillin in n-propanol was sprayed on the TLC plate. The plate was heated for 10 min and observed under UV illumination at 254 nm. A second spray of 1% KOH in ethanol, followed by heating the plate again produced various colored spots.

Lipids: The spray consisted of 0.1 g ferric chloride and 7 g sulfosalicylic acid dissolved in 25 mL water and then diluted to 100 mL with 95% ethanol. With fluorescent illumination lipids appear as white spots visible on purple background.

Organic acids: Solution A was prepared by dissolving 0.17 g silver nitrate in 1 mL water, adding 5 mL ammonia and diluting to 200 mL with ethanol. Solution B consisted of 6.5 g pyrogallol in 100 mL ethanol. The TLC plates were sprayed with solution A followed by solution B. Appearance of a spot(s) indicates the presence of organic acids.

Alcohols: The spray was prepared by dissolving 3 g vanillin in 100 mL absolute ethanol and adding 0.5 mL concentrated sulfuric acid. The plates were sprayed and heated at 120° F. Higher alcohols and ketones produce a blue-green spot.

TABLE 2

Composition of Fraction 8 Determined by TLC with Selective Chemical Reagents

| Compound Detected | TLC Plate | | | | | | | | | |
|---|---|---|---|---|---|---|---|---|---|---|
| | 1 | 2 | 3 | 4 | 5 | 6 | 7 | 8 | 9 | 10 |
| Tannin | + | + | + | + | + | + | + | + | + | + |
| Procyanidin | + | + | + | + | + | + | + | + | + | + |
| Hydrolyzable tannin | − | − | − | − | − | − | − | − | − | − |
| Alkaloid | − | − | − | − | − | − | − | − | − | − |
| Carbohydrate | − | − | − | − | − | − | − | − | − | − |
| Simple sugar | − | − | − | − | − | − | − | − | − | − |
| Protein | − | − | − | − | − | − | − | − | − | − |
| Lipid | − | − | − | − | − | − | − | − | − | − |
| Alcohol | − | − | − | − | − | − | − | − | − | − |
| Organic acid | − | − | − | − | − | − | − | − | − | − |

B. Anthocyanidin Formation

Two additional chemical tests were used to confirm the proanthocyanidin composition of Fraction 8: (1) the formation of anthocyanidins after treatment with n-butanol-HCl (Govindarajan & Mathew, 1965, Phytochemistry 4:985–988), and (2), color formation with absorbance at 500 nm following sulfuric acid-catalyzed condensation of vanillin with the phloroglucinol ring (Swain & Hillis, 1959, J. Sci. Food Agric. 10:63–68).

C. HPLC

High performance liquid chromatography (HPLC) was also employed to demonstrate the purity of the proanthocyanidin extract, Fraction 8 from mature red fruit. The extract was injected onto an analytical C-8 column (Zorbax 300SB 4.6 mm×25 cm, MacMod Analytical) and run using a gradient pump with a mobile phase of 100% methanol. Absorbance was measured using a photodiode array detector (Dionex Corp.) that detected all wavelengths simultaneously.

Figure 2:
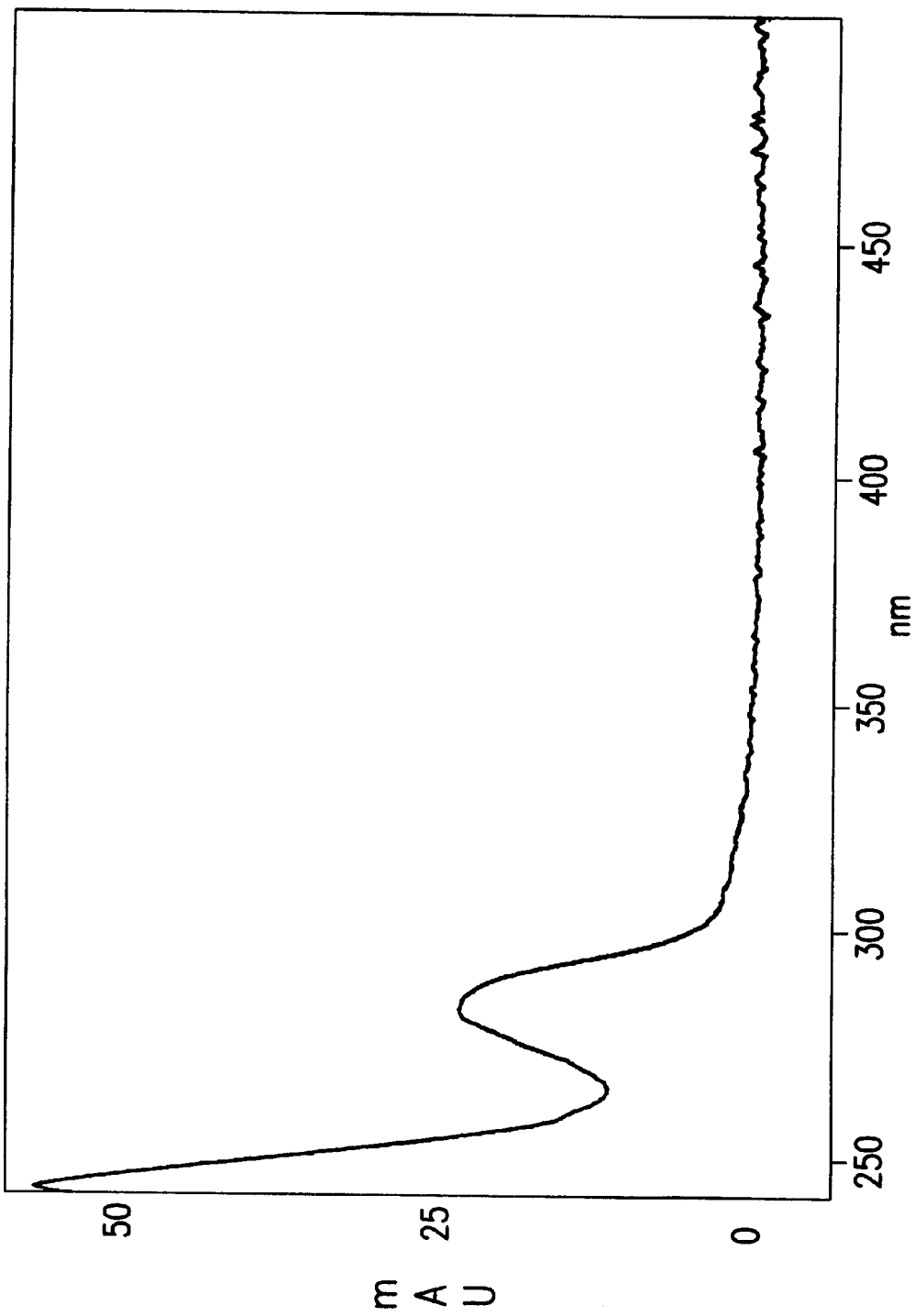
FIG. 2 depicts an absorbance spectrum from 230 to 550 nm of a proanthocyanidin extract (Fraction 8 of Example 1) after further purification by HPLC with diode array detection using an analytical C-8 column eluted with 100% methanol.
Figure 3A:
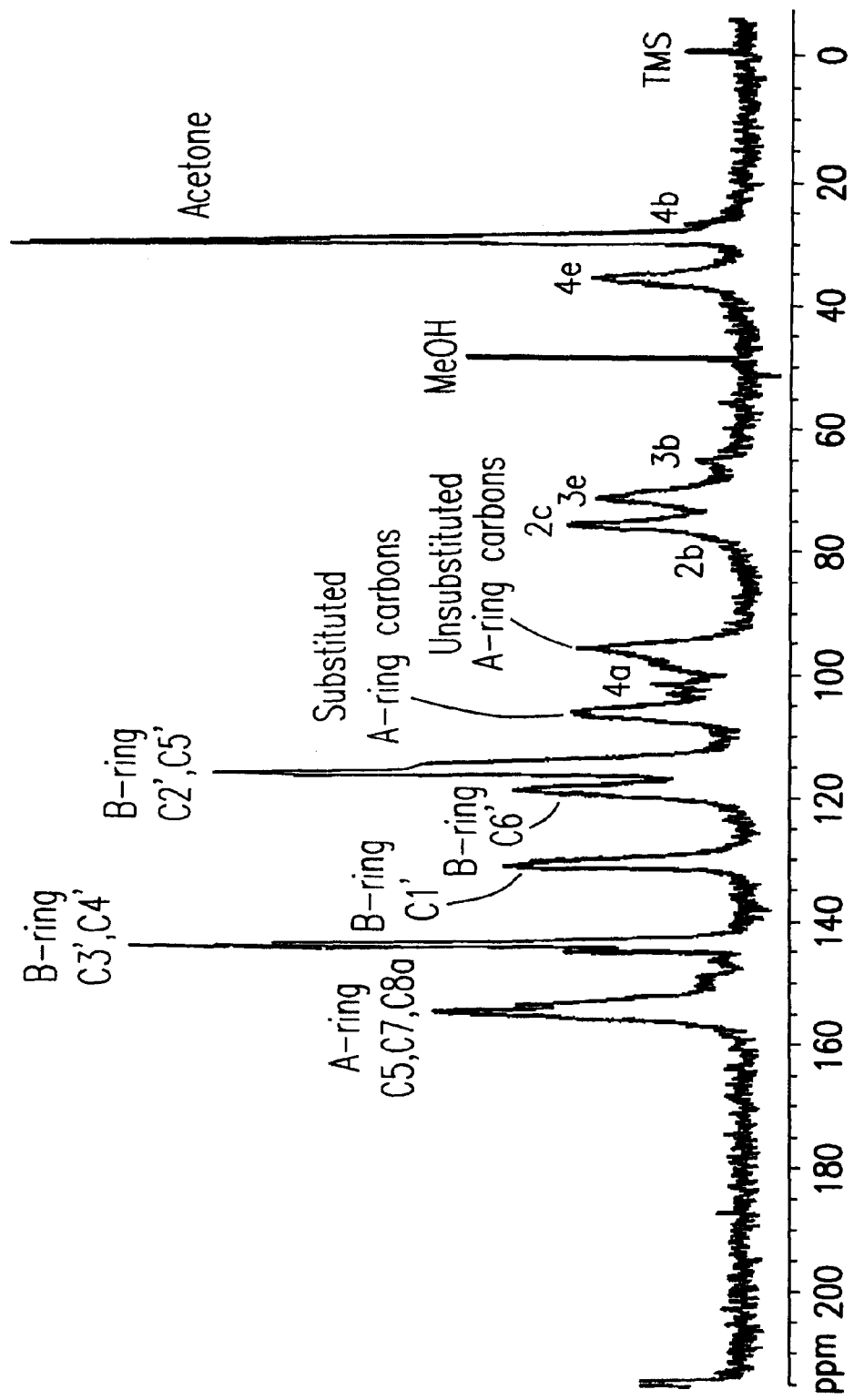
FIG. 3A depicts a $^{13}$C-NMR spectrum of the proanthocyanidin extract of Fraction 8*a* of Example 1.
Figure 3B:
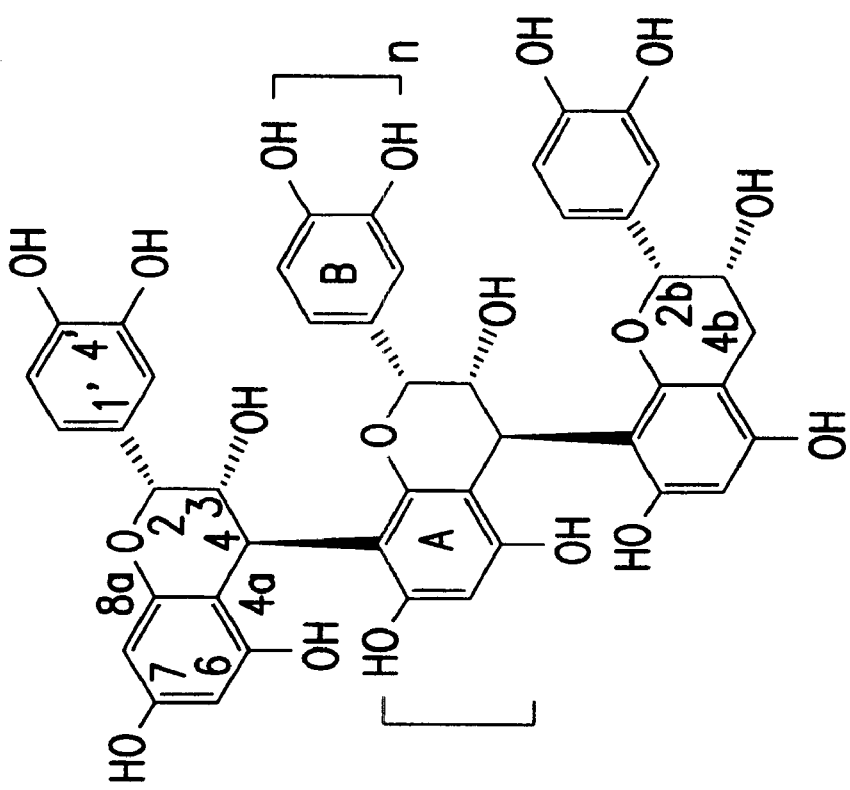
FIG. 3B shows the chemical structure of all B-linked proanthocyanidin having 4 or more flavanoid monomer units.
Figure 3C:
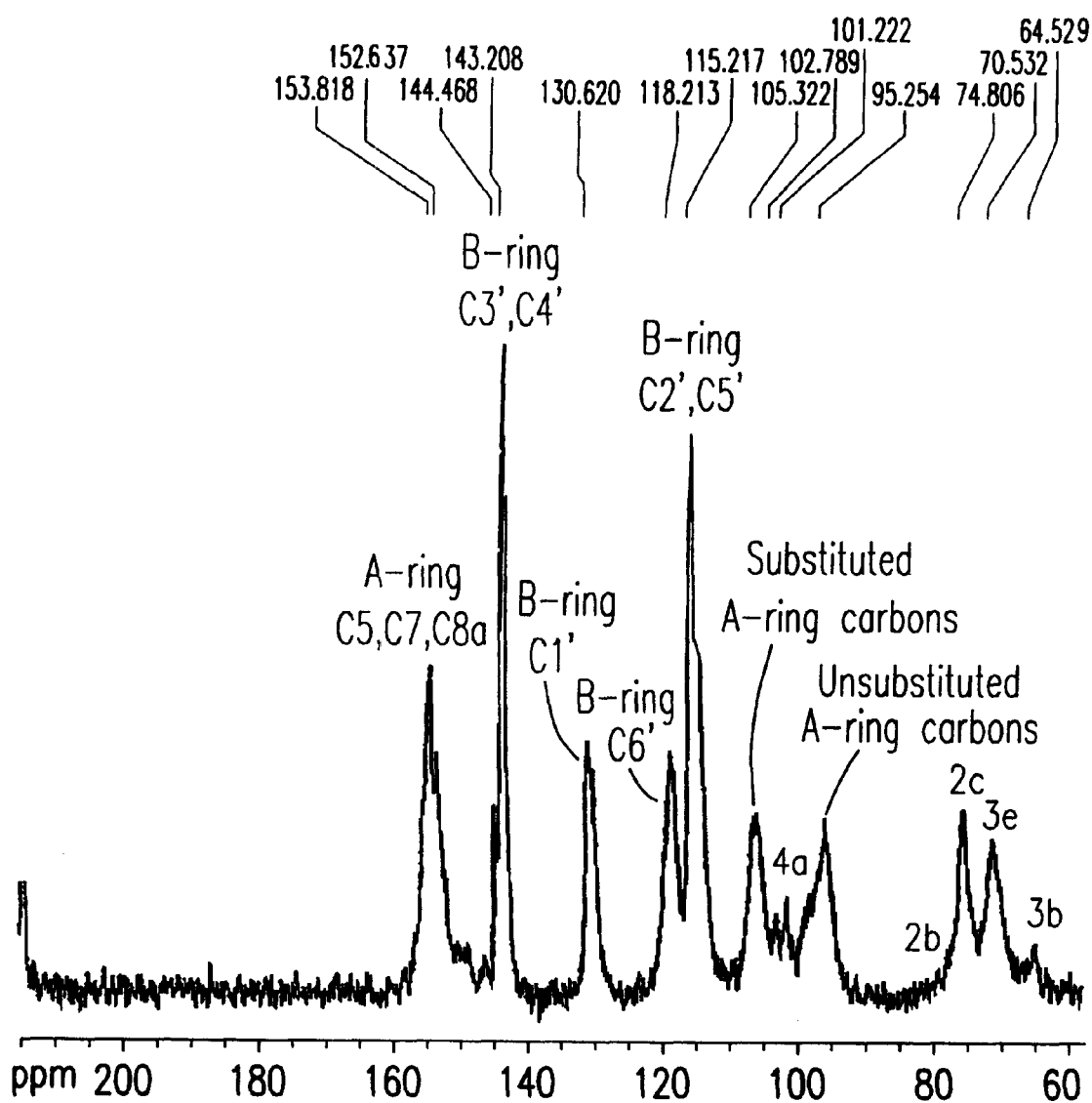
FIGS. 3C and 3D depict the $^{13}$C-NMR spectrum of FIG. 3A in expanded form, where
Figure 3D:
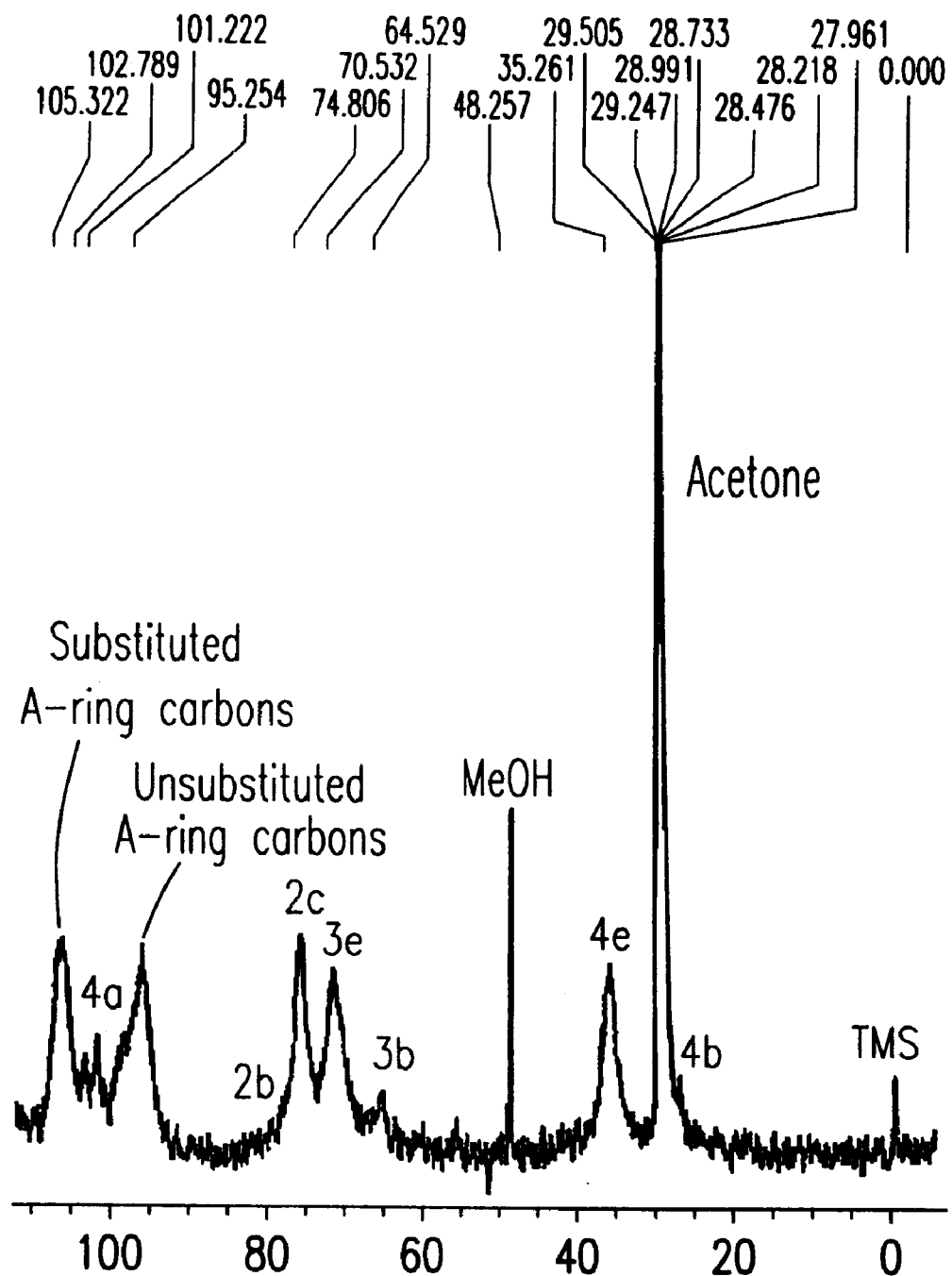
Figure 4A:
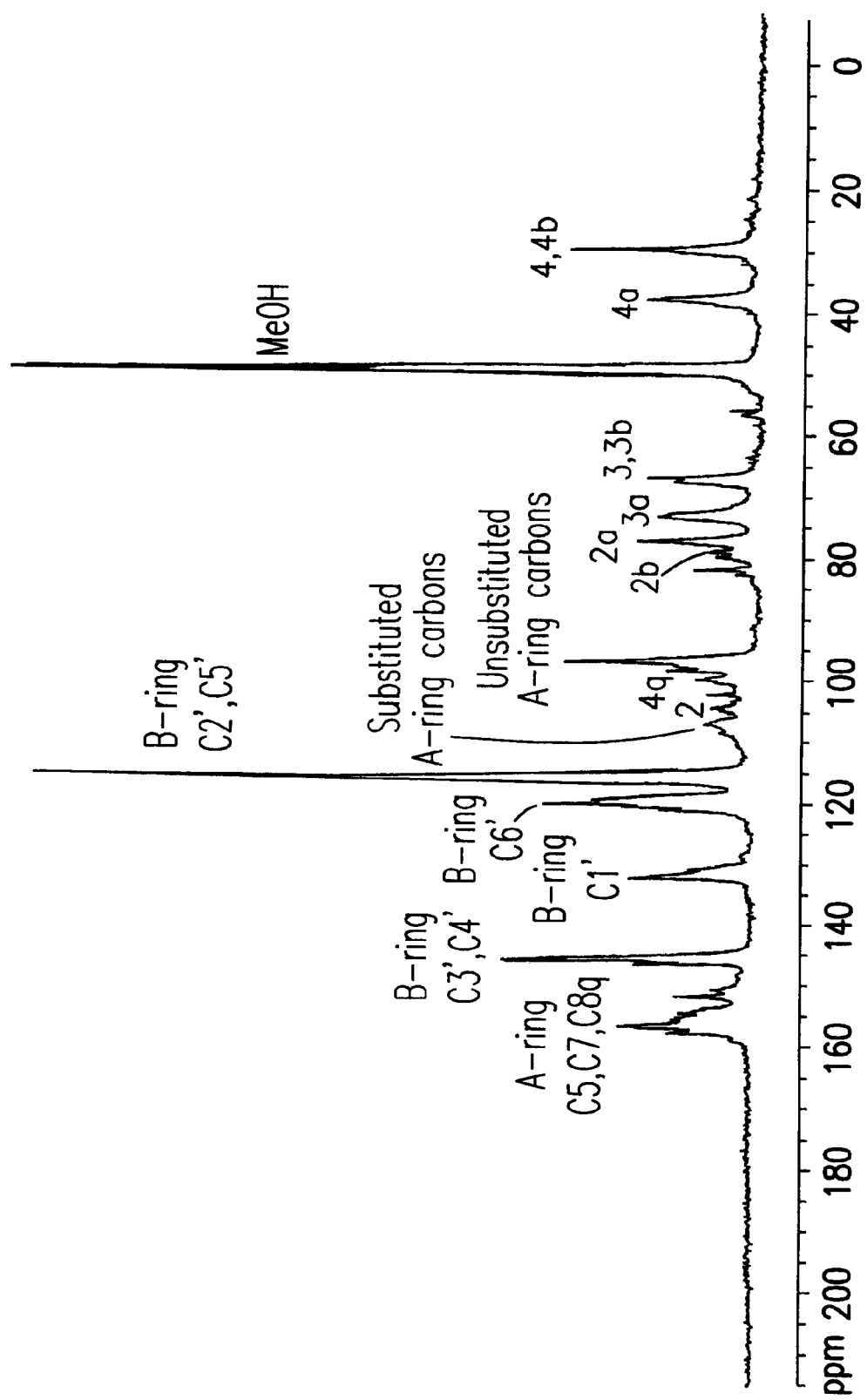
FIG. 4A depicts a $^{13}$C-NMR spectrum of the proanthocyanidin extract of Fraction 8*b* of Example 1.
Figure 4B:
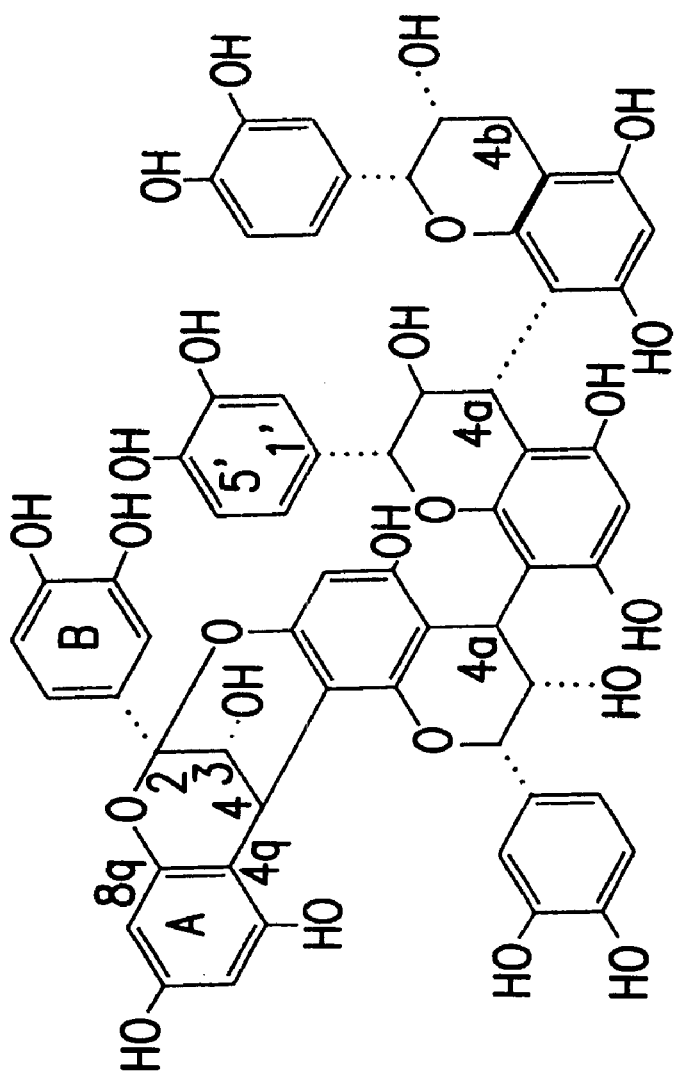
FIG. 4B shows the chemical structure of an A-linked proanthocyanidin.
Figure 4C:
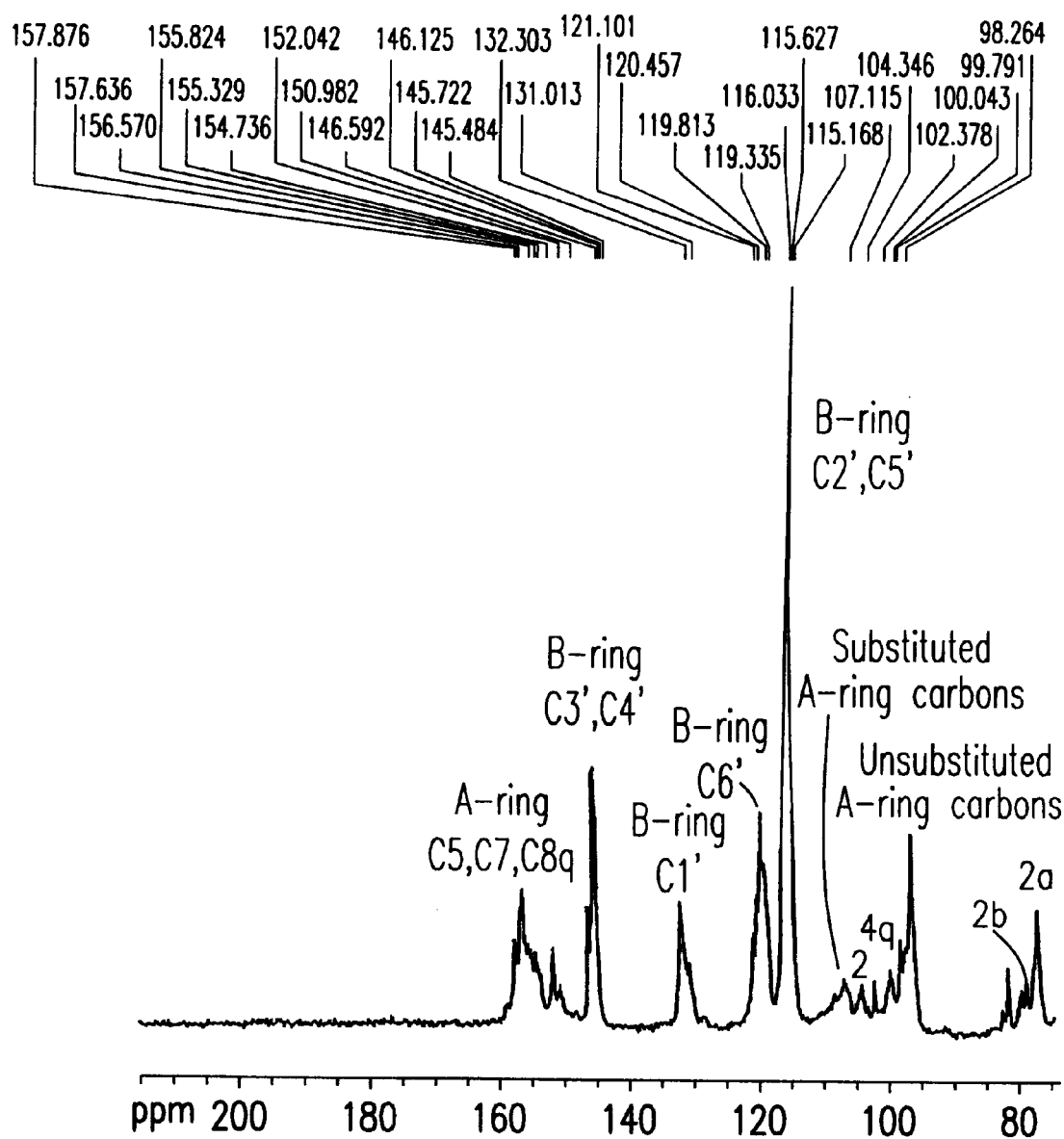
FIGS. 4C and 4D depict the $^{13}$C-NMR spectrum of FIG. 4A in expanded form, where
Figure 4D:
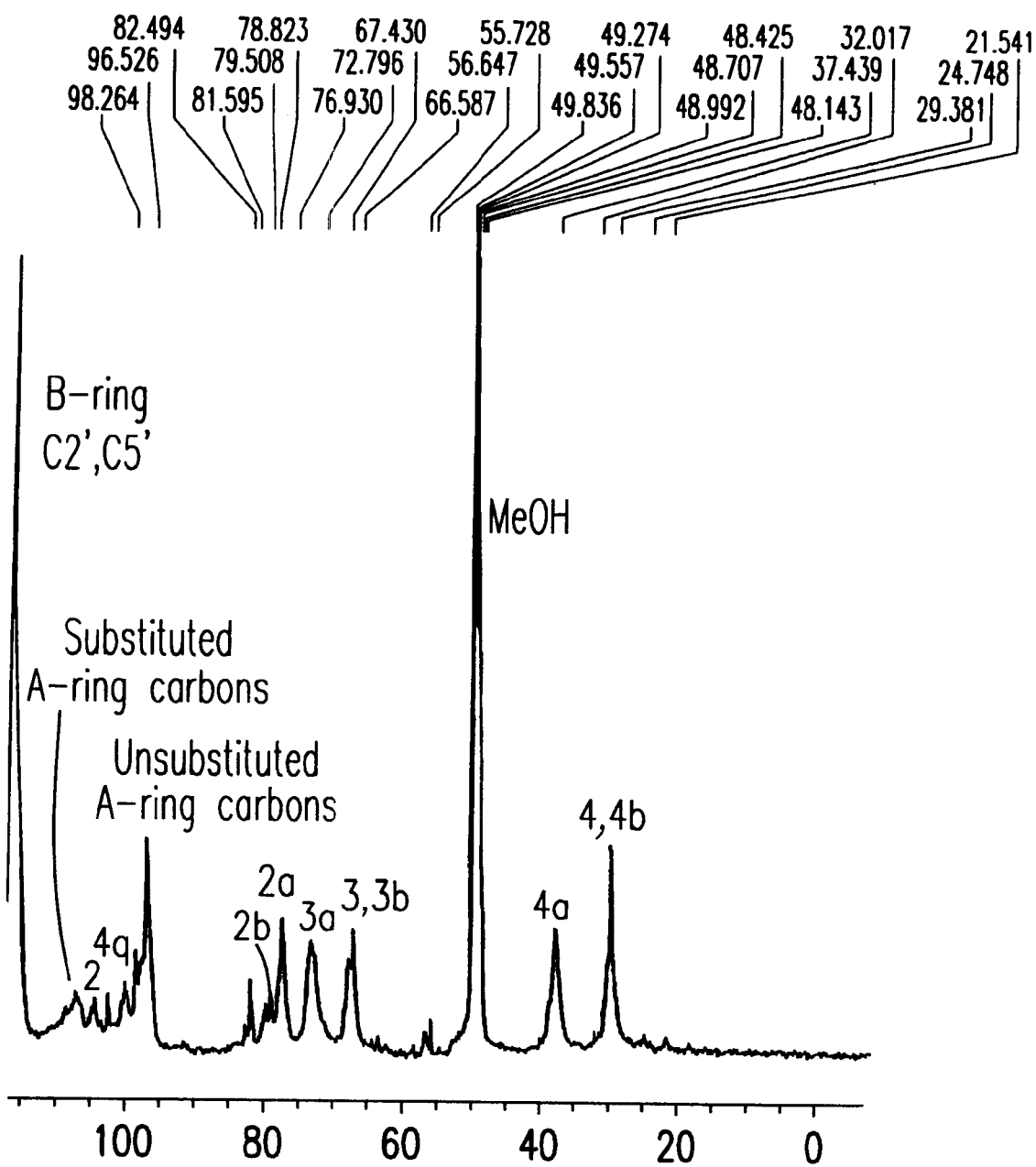

The absorbance spectrum (230 to 550nm) of Fraction 8 showed absorption at 280 nm, which is characteristic of proanthocyanidins (FIG. 2). There was no absorption in the 360 or 550 nm range, which would be indicative of the presence of flavonols or anthocyanin compounds, respectively.

D. $^{13}$C-NMR Spectroscopy

The $^{13}$C-NMR spectrum of Fraction 8a and 8b (Example 1) was performed on a Bruker Avance 300 model at 75 MHZ and referenced to TMS. Spectra were obtained using a 5 mm quard nuclear probe with a zgpg 30 pulse sequence with proton wartz decoupling and acquisition time set at 0.865 seconds with a delay time of 0.50 seconds. The total number of scans was 7500.

Fraction 8a (the water-soluble fraction) consisted of a proanthocyanidin mixture where all signals of any significance could be attributed directly to the constitutive procyanidin flavanoid units (FIG. 3). Procyanidin flavanoid units are characterized by a three ring system consisting of an aromatic A-ring based on phloroglucinol hydroxylation pattern, a pyran C-ring fused to the A-ring and an appending catechol B-ring attached to C2 of the pyran ring. The absence of other carbon resonances in the spectrum indicated that the sample consisted of pure procyanidin derivatives. The $^{13}$C-NMR spectrum of Fraction 8a was fully in accord with this chemical structure.

The oxygenated aromatic carbons C5, C7, and C8a of the A-ring were evident in the low field region of the spectrum (150–158 ppm), while those similarly substituted carbons (C3' and C4') of the B-ring were observed at 142–145 ppm, and those of the aliphatic pyran ring (C3) were found higher upfield at 64–74 ppm. The observation of the remaining carbon resonances at 94–108 ppm for C4a, C6 and C8 of the A-ring, at 114–132 ppm for C1', C2', C5', and C6' of the B-ring, and at 27–38 ppm for C4 of the C-ring fully accounted for all the carbon atoms of the flavanoid constitutive units. These flavanoid units were linked together as proanthocyanidins as confirmed by the presence of diagnostic carbon peaks at about 36 ppm and 106 ppm for the inter-flavanoid-linked carbons C4 and C6/C8, respectively. The ratio of the 66 ppm peak area (C3 of bottom unit) to that of the 72 ppm peak area (C3 of extender units) is about 1:5.4 suggesting that the average chain length is between 6 and 7 epicatechin units.

Procyanidins consist of catechin and/or epicatechin flavanoid units. The distinguishing feature between a catechin and epicatechin unit is the low field position (80–84 ppm) of the C2 carbon chemical shift associated with the 2,3-trans configuration of the catechin unit compared to the more upfield position (75–79 ppm) of the C2 carbon chemical shift associated with the 2,3-cis configuration of the epicatechin unit. Fraction 8a exhibits only the higher field signals (75–79 ppm), indicating that these procyanidins are predominantly epicatechin units.

The $^{13}$C-NMR spectrum of Fraction 8b (FIG. 4), representing the purified ethyl acetate-soluble fraction, was fully consistent with that of a proanthocyanidin oligomer where all the major carbon signals could be directly attributed to the constitutive flavanoid units as detailed above for the proanthocyanidins from the water-soluble fraction. However, there were some significant differences in the fine structure of the carbon chemical shifts between the two $^{13}$C-NMR spectra, the most apparent being the appearance of new multiple peaks between 78 ppm and 82.5 ppm consistent with the C2 of terminating flavanoid units and the upfield position of some hydroxylated A-ring carbons at 150 to 152 ppm. The latter shifts are characteristic of the oxygenated carbons of the A-ring involved in the A-type linkages. Another probable indication of the presence of the A-type linkages in the sample was the unexpected signal size at 66–67 ppm usually attributed to the C3 of the terminating flavanoid unit, so much so that this signal area was comparable to that of the extender C3 at 72.8 ppm. This observation would have suggested a dimeric structure but the broad nature of the signals ruled this out because in A-type linkages, the new ether bond formed at C2 causes an upfield shift of the C3 signal of the extender unit to the general region around 67 ppm. This shift can account for the additional size of the signal observed in that region.

Additional evidence for the presence of the A-type linkage was obtained from H,C-COSY NMR data (HMQC). In A-type linkages the chemical shift of C4 of the "upper" C-ring coincides with that of the C4 from the terminal unit in the proanthocyanidin polymer, however, these two carbons can be distinguished by the chemical shift of their respective attached protons in which the chemical shift of the proton on the A-type C4 is generally observed downfield between 4 to 5 ppm while the proton of the C4 extender unit is observed upfield around 3 ppm. The HMQC spectrum of Fraction 8b showed that those carbons with a chemical shift around 29.4 ppm in the $^{13}$C-NMR spectrum had proton resonances at 4.23 ppm and 2.90 ppm and thus indicated the presence of an A-type linkage in this proanthocyanidin oligomer.

Moreover, the peak area of the C3 chemical shifts around 67 and 72 ppm were in the ratio of about 1 to 1.29, suggesting that there is one terminal unit to just over 3 extender units with the chemical shift from one of the extender units being located in the C3 terminal unit because of the presence of an A-type linkage.

Figure 5:
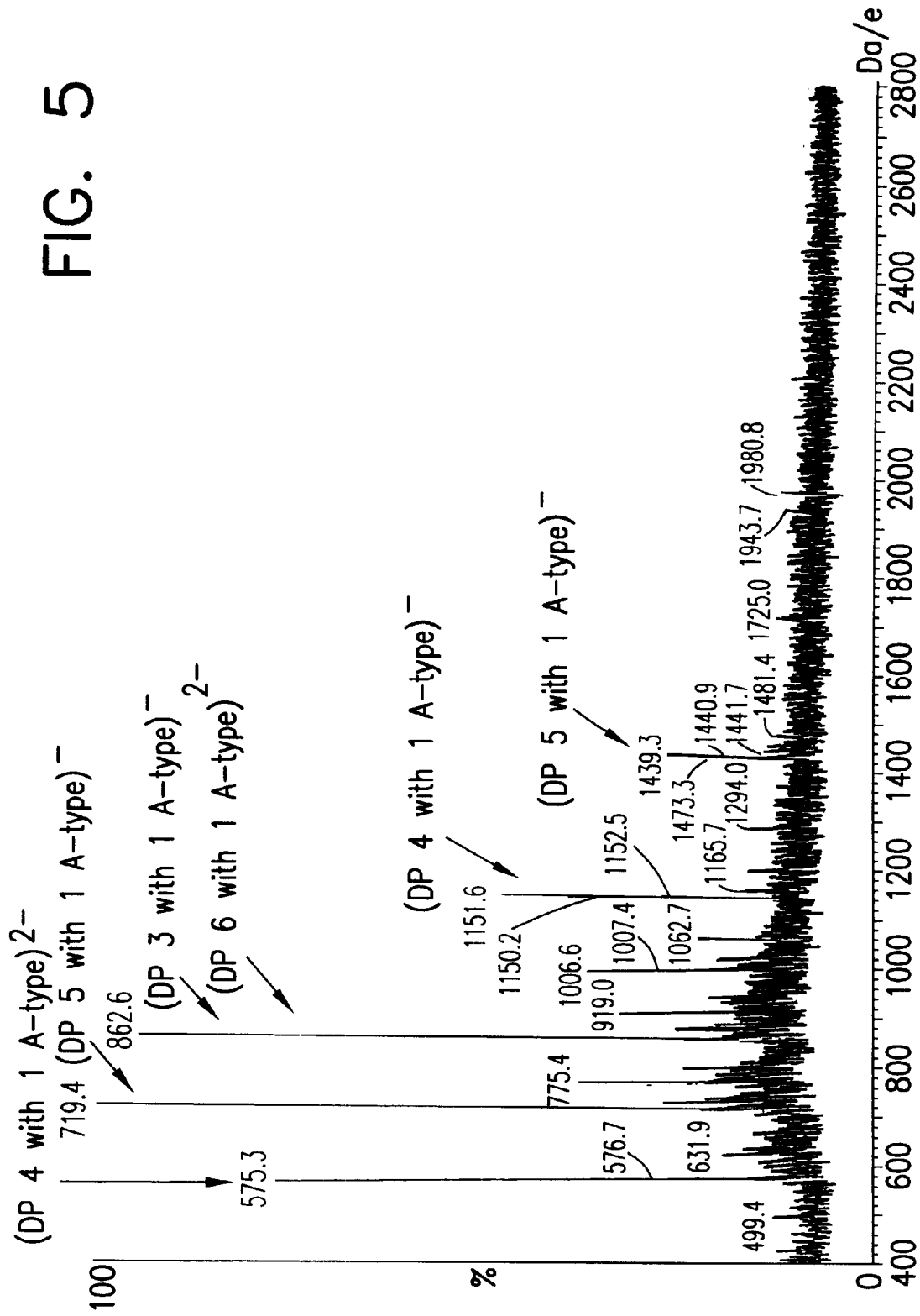
FIG. 5 depicts the electrospray ionization mass spectrum of the proanthocyanidin extract of Fraction 8*b* of Example 1.

This structure was further confirmed by electrospray ionization mass spectrometry (ESI-MS) as shown in FIG. 5. Two main moleculer negative ion peaks were observed at m/z 1151 and 1439 and are attributable to a tetramer and pentamer, respectively, containing one A-type interflavanoid linkage. In addition, the smaller peak at higher mass m/z 1725 suggested the sample also contained a small amount of a proanthocyanidin hexamer with two A-type interflavanoid linkages. Negative ion peaks observed at lower mass were also fully consistent with these results where the peak at m/z 862.8 is a trimer with one A-type linkage (charge −1) or a hexamer with one A-type linkage (charge −2), the peak at m/z 719.4 is a pentamer (charge −1) with one A-type linkage and the peak at m/z 575.3 is a tetramer (charge −1) with one A-type linkage.

EXAMPLE 3

Bioactivity of Proanthocyanidin Extracts

A. Bacterial Strains

Sixty *E. coli* strains were isolated from the urine of human and animal (dog and cat) patients suffering from urinary tract infections. After determining the fimbrial type of each strain, 5 strains specific for P-type fimbriae, and 5 strains specific for type 1 fimbriae were selected for use in bioactivity testing. Bacterial strains were subcultured in tryptose broth at 37° C. for 16 h. P-type strains were transferred to colonization factor agar (CFA) plates and grow n overnight at 37° C. to enhance production of P-type fimbriae. Strains were harvested by centrifugation, washed once and suspended in phosphate-buffered saline solution (PBS) at pH 7.0 at a concentration of 5×10$^8$ bacteria/mL. The individual phenotypic strains were tested in each of the following bioassays and did not differ significantly in their ability to agglutinate red blood cells or yeast. Therefore, mixtures of P-type strains were used to test for P-type bioactivity, and mixtures of type 1 strains were used to test for type 1 bioactivity. Strains were kept frozen at −70° C. in tryptose broth (30% glycerol) for long-term storage.

B. Inhibition of Adherence Bioassay for P-type *E. coli*

1. Hemagglutination Assay

Red blood cells donated by human volunteers with A+ blood type (HRBC) were suspended at a concentration of 3% HRBC. Fractions to be tested for bioactivity were suspended in PBS and adjusted to neutral pH with 1 M NaOH. The bioassay should be performed under neutral conditions, otherwise the assay leads to false-positive readings at low pH (<4) and high pH (>8) in the bioassay (Table 3).

Dried Fractions 1–8 from Example 1 were rehydrated in PBS, neutralized, and tested for ability to inhibit agglutination of HRBC. Diluted fractions (30 μl) were incubated with 10 μl of a P-type bacterial suspension in a 24-well polystyrene plate for 10 min on a rotary shaker. HRBC (10 μl) were added to each well and incubation continued for 20 min on a rotary shaker. Controls which showed no agglutination or complete inhibition of agglutination included (1) bacteria only (2) HRBC only, (3) bacteria and test fraction and (4),bacteria, HRBC and epicatechin trimer, a proanthocyanidin standard. The control to show agglutination consisted of bacteria and HRBC.

The ability of each fraction to inhibit bacterial adherence in this assay was assessed microscopically and is provided in Table 4 under the column "HRBC". A "+" indicates that the fraction inhibited P-type adherence and a "−" indicates that no adherence was observed.

To compare the bioactivity of proanthocyanidin extracts from leaves and fruit (mature and immature), serial (2-fold) dilutions of Fractions 1 and 8 were made using equivalent amounts of material obtained from 1 g of starting material (fresh weight). Thus, for ripe fruit 10.72 mg of Fraction 1 or Fraction 8 were dissolved in 1 mL PBS to prepare the undiluted solution subjected to the serial dilution. Similar preparations were made for unripe fruit using 12.14 mg and for leaves using 21.16 mg. The relative agglutination in the dilution series was recorded by microscopic observation of the agglutination reaction and scored on a scale of 0 to 3 with a score of 0 representing 95–100% of HRBC agglutinated (no inhibition of agglutination by the test fraction), a score of 1 representing 50–95% of HRBC agglutinated, a score of 2 representing 5–50% of HRBC agglutinated, and a score of 3 representing less than 5% of the HRBC agglutinated, i.e., total inhibition of agglutination by the test fraction. The results provided in Table 5 demonstrate that the cranberry plant leaves contain more proanthocyanidins than fruit on a fresh weight basis and are more active in inhibiting P-type *E. coli* to HRBC than the proanthocyanidins extracted from the cranberry fruit.

2. Latex Bead Agglutination Test

The fractions were also tested in the P-type receptor bioassay of de Man et al., 1987, J. Clin. Microbiol. 25(2):401–406. Dried Fractions 1–8 were dissolved in PBS, neutralized, and mixed with P-type bacterial suspensions (30 μl fraction to 10 μl of bacterial suspension) on a polystyrene 24-well plate and incubated for 10 min on a rotary shaker. Latex beads coated with a synthetic P-type receptor analog (Galα1→4Galβ) (BACH test, Kabi Vitrum, Stockholm, Sweden) suspended in water at a concentration of 5×109 beads/mL were added (10 μl) to each well and incubation continued for 20 min on the rotary shaker. Controls which showed no agglutination or complete inhibition of agglutination included (1) bacteria only (2) bacteria and uncoated beads, (3) bacteria and test fraction, (4) uncoated beads and test fractions, and (5) bacteria, coated beads and epicatechin trimer. The control to show agglutination consisted of bacteria and coated beads. The relative ability of each fraction to inhibit bacterial adherence in this assay was assessed microscopically and is provided in Table 4 under the column "P-receptor". A "+" indicates that the fraction inhibited P-type adherence and a "−" indicates that no adherence was observed.

C. Inhibition of Adherence Bioassay for Type 1 *E. coli*

1. Hemagglutination Assay

The inhibition of adherence of type 1 *E. coli* by the various fractions was tested according to hemagglutination assay for P-type bacteria, except guinea pig red blood cells (GPRBC) were used in place of HRBC. The results are shown in Table 4 under the column GPRBC using the same scoring system as described above.

2. Yeast Agglutination Assay

The fractions were also tested in the bioassay of Eschdat et al., 1978, Biochem. Biophys. Res. Commun. 85:1551–1559, using yeast cells. Yeast cultures of *Saccharomyces cerevisiae* were grown in Sabouraud dextrose broth and incubated for 24 hr at 38° C. Yeast cells were transferred to Sabouraud dextrose agar plates and grown under the same conditions. Cells were harvested, washed and suspended in PBS at a concentration of $4 \times 10^8$ cells/mL. Ten μl of type 1-fimbriated *E. coli* were mixed with neutralized test fractions (30 μl) in a 24-well polystyrene plate and incubated for 10 min on a rotary shaker. Yeast cell suspension (10 μl) was added to each well and incubated for 5 min. Controls which showed no agglutination or complete inhibition of agglutination included (1) bacteria only (2) yeast only, (3) bacteria and test fraction and (4) bacteria, yeast and 1% D-mannose. The control to show agglutination consisted of bacteria and yeast. The results are shown in Table 4 under the column "Yeast Cells" using the same scoring system as described above.

TABLE 3

Agglutination Response as a Function of pH for P-type *E. coli*

| Buffer pH | Agglutination Response |
| --- | --- |
| 2 | − |
| 3 | − |
| 4 | +/− |
| 5 | + |
| 6 | + |
| 7 | + |
| 8 | +/− |
| 9 | − |
| 10 | − |

TABLE 4

Inhibition of Agglutination of P-type and Type 1 *E. coli* by Extracted Cranberry (*V. macrocarpon*) Fractions

|  | HRBC | P-Receptor | GPRBC | Yeast Cells |
| --- | --- | --- | --- | --- |
| 1- Clarified Whole Extract | + | + | + | + |
| 2- Sugars | − | − | + | + |
| 3- Acids | − | − | − | − |
| 4- Total Polyphenolics | + | + | − | − |
| 5- Lipids, Waxes | − | − | − | − |
| 6- Polyphenolics, Sugars, Acids | + | + | + | + |
| 7- Flavonols, Anthocyanins | − | − | − | − |
| 8- Proanthocyanidins | + | + | − | − |
| Controls |  |  |  |  |
| 1% D-Mannose | − | − | + | + |
| Epicatechin Trimer | + | + | − | − |

TABLE 5

Relative Inhibition of P-type *E. coli*-induced HRBC Agglutination by Cranberry Extracts

| | Unfractionated Extract | | | Proanthocyanidin Extract | | |
| --- | --- | --- | --- | --- | --- | --- |
| Dilution | Ripe Fruit | Unripe Fruit | Leaves | Ripe Fruit | Unripe Fruit | Leaves |
| 1:1 | 3 | 3 | 3 | 3 | 3 | 3 |
| 1:2 | 3 | 3 | 3 | 3 | 3 | 3 |
| 1:4 | 3 | 3 | 3 | 3 | 3 | 3 |
| 1:8 | 1 | 2 | 3 | 3 | 3 | 3 |
| 1:16 | 0 | 0 | 3 | 3 | 3 | 3 |
| 1:32 | 0 | 0 | 2 | 2 | 3 | 3 |
| 1:64 | 0 | 0 | 0 | 2 | 3 | 3 |
| 1:128 | 0 | 0 | 0 | 1 | 2 | 3 |
| 1:256 | 0 | 0 | 0 | 0 | 0 | 3 |
| 1:512 | 0 | 0 | 0 | 0 | 0 | 0 |

We claim:

1. A proanthocyanidin composition comprising proanthocyanidin compounds having an average of from at least four to about seven epicatechin flavanoid units, wherein each proanthocyanidin compound has at least two of said units are linked together by an A-type interflavanoid linkage by bonds between C4 and C8 and between C2 and the oxygen of C7 of the units, and the remainder of the units are linked to each other by a B-type interflavanoid bond between C4 and C8 or between C4 and C6 of the units.

2. A food composition comprising a consumable carrier in admixture with the proanthocyanidin composition of claim 1.

3. The composition of claim 1, wherein said compounds consist of an average of four, five or six epicatechin flavanoid units.

4. A pharmaceutical composition comprising the proanthocyanidin composition of claim 1 or 3 and a pharmaceutically acceptable carrier.

5. The food composition of claim 2 wherein said consumable carrier is livestock feed.

6. The food composition of claim 2 wherein said consumable carrier is domestic animal feed.

7. The food composition of claim 2 wherein said consumable carrier is a consumable food product.

8. The composition of claim 7, wherein said consumable food product is a cranberry-containing food product.

9. The composition of claim 8, wherein said cranberry-containing food product is a dried cranberry, a sweetened and dried cranberry, a flavored fruit piece, a sauce, a jelly, a relish, juice, wine or a cranberry juice-containing product.

10. The composition of claim 7, wherein said consumable food product is a beverage.

11. The composition of claim 10, wherein said beverage comprises cranberry juice, unpasteurized juice or pasteurized juice.

12. The food composition of claim 7, wherein said consumable food product is ground meat.

\* \* \* \* \*

UNITED STATES PATENT AND TRADEMARK OFFICE
CERTIFICATE OF CORRECTION

PATENT NO. : 6,608,102 B1
DATED : August 19, 2003
INVENTOR(S) : Howell et al.

It is certified that error appears in the above-identified patent and that said Letters Patent is hereby corrected as shown below:

Column 22,
Line 26, please delete the word "are".

Signed and Sealed this

Twentieth Day of April, 2004

JON W. DUDAS
*Acting Director of the United States Patent and Trademark Office*